(12) United States Patent
Lee et al.

(10) Patent No.: US 12,011,562 B2
(45) Date of Patent: Jun. 18, 2024

(54) CARTRIDGE AND APPLICATOR FOR DRUG DELIVERY AND MICRONEEDLE PATCH USED THEREFOR

(71) Applicant: JUBILEE BIOTECH CO., LTD., Gunpo-si (KR)

(72) Inventors: Sung Kyoung Lee, Seoul (KR); Goong Hyun Han, Siheung-si (KR); Chan Sik Yoon, Yongin-si (KR)

(73) Assignee: Jubilee Biotech Co., Ltd., Gunpo-si (KR)

( * ) Notice: Subject to any disclaimer, the term of this patent is extended or adjusted under 35 U.S.C. 154(b) by 0 days.

(21) Appl. No.: 18/127,599

(22) Filed: Mar. 28, 2023

(65) Prior Publication Data

US 2023/0233825 A1 Jul. 27, 2023

Related U.S. Application Data

(63) Continuation of application No. 17/893,086, filed on Aug. 22, 2022, which is a continuation of application No. PCT/KR2021/002145, filed on Feb. 19, 2021.

(60) Provisional application No. 62/979,224, filed on Feb. 20, 2020.

(30) Foreign Application Priority Data

Sep. 11, 2020 (KR) .................. 10-2020-0116801

(51) Int. Cl.
*A61M 37/00* (2006.01)
(52) U.S. Cl.
CPC . *A61M 37/0015* (2013.01); *A61M 2037/0023* (2013.01); *A61M 2205/33* (2013.01)

(58) Field of Classification Search
CPC ...... A61M 37/0015; A61M 2037/0023; A61M 2205/33
USPC ........................................................ 604/131
See application file for complete search history.

(56) References Cited

U.S. PATENT DOCUMENTS 9,603,562 B2 * 3/2017 Aceti ................. A61B 5/15146

FOREIGN PATENT DOCUMENTS

| EP | 1299147 B1 | 8/2006 |
| JP | 6158838 B2 | 7/2017 |
| JP | 6193409 B2 | 9/2017 |

(Continued)

OTHER PUBLICATIONS

International Search Report dated Jun. 18, 2021 in International Patent Application No. PCT/KR2021/002145.

(Continued)

*Primary Examiner* — Phillip A Gray
(74) *Attorney, Agent, or Firm* — Knobbe, Martens, Olson, & Bear, LLP

(57) ABSTRACT

Proposed is a cartridge (1000) for accommodating a microneedle patch (100) comprising: a body portion (1002) which is accommodated in an accommodating part formed in a housing (201) of an applicator (200), and a flat plate portion (1004), mounted on the body portion (1002), comprising a flat plate opening (1006) through which a pressurizing part (404) of a drive mechanism (400) passes and a fixing portion (1005) operatively coupled to the drive mechanism (400), wherein the flat plate portion (1004) is rotated according to a driving of the drive mechanism (400) and is located below the microneedle patch (100) to supports the microneedle patch (100).

3 Claims, 27 Drawing Sheets

(56) References Cited

FOREIGN PATENT DOCUMENTS

| KR | 10-2010-0064669 A | 6/2010 |
|---|---|---|
| KR | 101746048 B1 | 6/2017 |

OTHER PUBLICATIONS

Written Opinion dated Jun. 18, 2021 in International Patent Application No. PCT/KR2021/002145.
Office Action dated Oct. 26, 2022 in Korean Patent Application No. 10-2020-0116801.

\* cited by examiner

1

210

504

404

PRESSURIZING STATE
AT SECOND POSITION

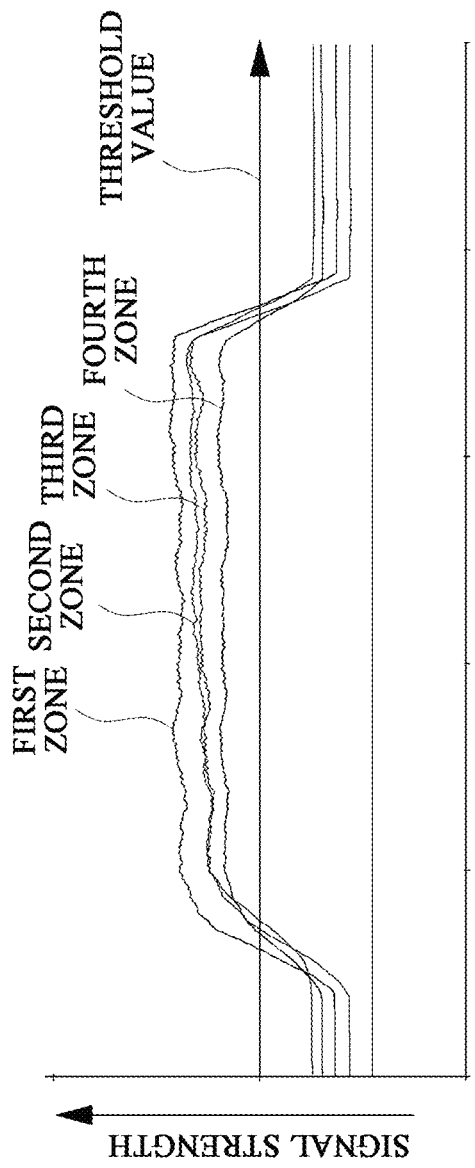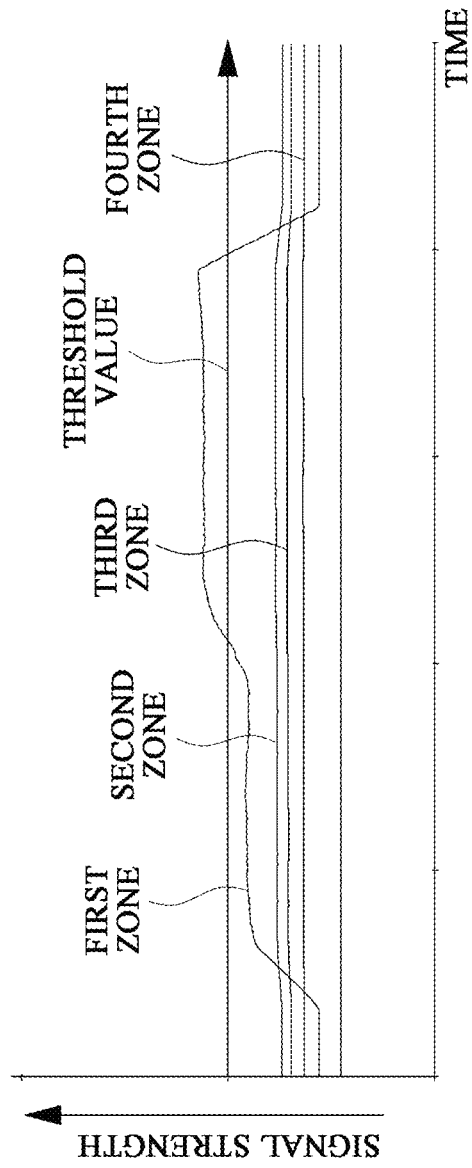

CARTRIDGE AND APPLICATOR FOR DRUG DELIVERY AND MICRONEEDLE PATCH USED THEREFOR

TECHNICAL FIELD

The present disclosure relates to a cartridge and an applicator for drug delivery and a microneedle patch used therefor.

BACKGROUND ART

The conventional drug injection method using a syringe has problems such as the need for a healthcare professional to administer an injection and the pain accompanying the injection. To solve these problems, a microneedle type drug injection system was developed.

The microneedle is a system that delivers active ingredients into the skin through the stratum corneum, which is the skin barrier layer. It is a new system that combines the efficacy of a conventional syringe with the convenience of a patch and has made many technological advances in recent years.

Yet, in the case of the patch-type microneedle, there is a problem in that a user himself or herself has to attach the microneedle to the skin and inject the drug, so that the user's active attachment action is still required.

DISCLOSURE

Technical Problem

Accordingly, the present disclosure is proposed to solve the above-described problems and an objective of the present disclosure is to provide an applicator in the form of a wearable device that can automatically inject drugs using a microneedle patch.

Another objective of the present disclosure is to provide a microneedle patch that can be used multiple times and can be used in replaceable cartridges in combination with a wearable device.

Technical Solution

According to an embodiment of the present disclosure for achieving the objectives as described above, provided is a microneedle patch including a body in which at least one opening is formed, and a microneedle body which is disposed in the opening and has at least one microneedle formed therein, wherein when an external force is applied in a first direction, the microneedle body moves in the first direction so as to administer a drug in the microneedle to a user's skin.

Advantageous Effects

According to an embodiment of the present disclosure, the microneedle patch can be used multiple times by rotating since it moves to administer the drug when an external force is applied thereto and moves back to the original position thereof, and it is configured in a form that can be used in combination with a wearable device so that the drug can be injected in a way convenient for users.

DESCRIPTION OF DRAWINGS

FIGS. 27A and 27B are graphs illustrating an electrical signal measured by a touch sensor according to the mounting state of an applicator.

BEST MODE

Figure 1:
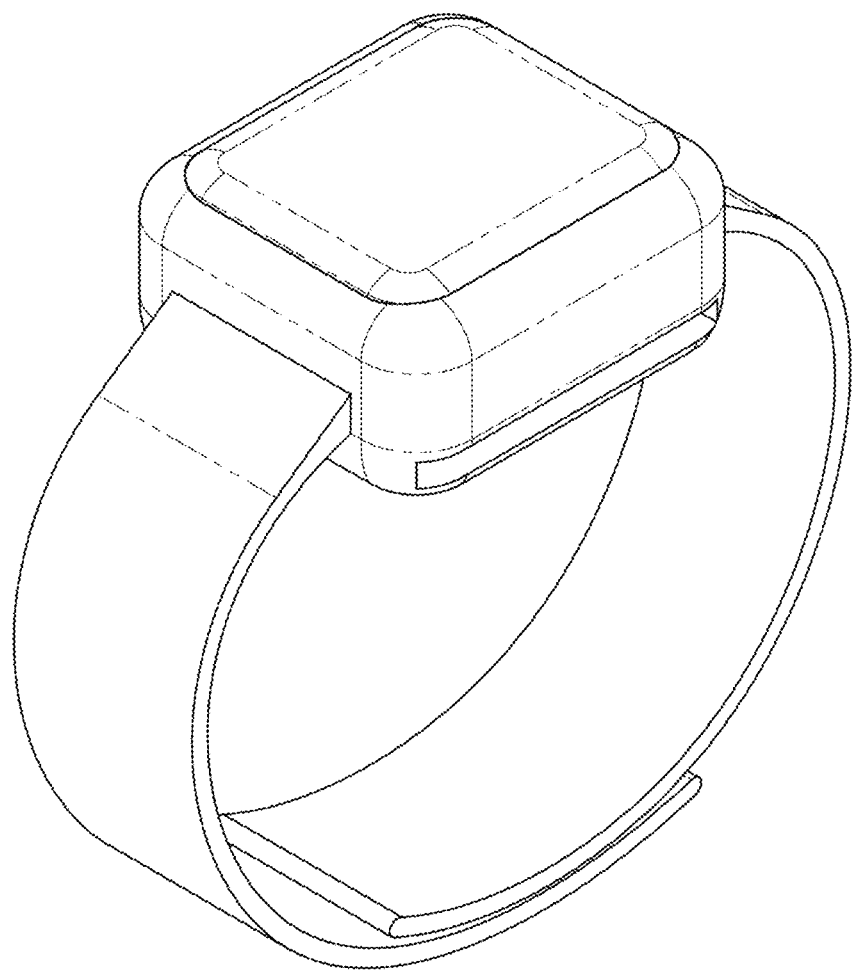
FIG. 1 illustrates the overall appearance of a drug delivery device according to an embodiment.

A microneedle applicator according to an embodiment includes: a patch delivery part configured to place a microneedle patch in a predetermined area; a housing having an cartridge accommodating part defined as a space for accommodating the cartridge and at least one opening; and a pressurizing part configured to apply a predetermined pressure to the microneedle patch, wherein the pressurizing part moves between a first position and a second position, and when the pressurizing part is at the second position, the pressurizing part comes into contact with the microneedle patch disposed in the predetermined area and applies the predetermined pressure to at least a portion of the microneedle patch, and the microneedle patch to which the predetermined pressure is applied is delivered directly to the skin through the opening.

MODE FOR INVENTION

Hereinafter, specific exemplary embodiments of the present disclosure will be described in detail with reference to the accompanying drawings. However, the spirit of the present disclosure is not limited to the embodiments presented, and those skilled in the art who understand the spirit of the present disclosure may be able to easily propose other conventional inventions or other embodiments that fall within the scope of the spirit of the disclosure by adding, changing, or deleting other elements within the scope of the same spirit, but this will also be included within the scope of the disclosure.

In addition, components that are the same in function within the scope of the same idea shown in the drawings of each embodiment will be described using the same reference numerals.

A microneedle applicator according to an embodiment includes: a first drive mechanism configured to operate to pressurize a microneedle patch; a second drive mechanism operatively connected with the first drive mechanism to change a posture of the first drive mechanism; and a controller configured to transmit a driving signal to the first and second drive mechanisms, wherein the first drive mechanism includes: a first driving motor; and a pressurizing part configured to pressurize at least one region of the microneedle patch by receiving power from the first driving motor, the second drive mechanism includes: a second driving motor; and a main gear connected with the first drive mechanism to rotate by receiving power from the second driving motor, the controller actuates the second drive mechanism so that the pressurizing part moves from a first position to a second position of the microneedle patch and actuates the first drive mechanism so that the pressurizing part pressurizes the microneedle patch on the second position, and the pressurizing part may execute translation movement by 1 displacement substantially vertically downward on a surface of the microneedle patch according to an operation of the first driving motor.

The second drive mechanism may be actuated for the pressurizing part to return from the second position to the first position.

The controller may actuate the second drive mechanism so that the pressurizing part returned to the first position moves to a third position and actuate the first drive mechanism so that the pressurizing part pressurizes the microneedle patch on the third position.

Also, the controller may actuate the second drive mechanism so that the pressurizing part returns from the third position to the first position.

When the second drive mechanism is actuated for the pressurizing part to move from the first position to the second position, the main gear may rotate by second displacement along a first direction according to an operation of the second driving motor.

When the second drive mechanism is actuated for the pressurizing part to return from the second position to the first position, the main gear may rotate by the second displacement along a second direction, which is different from the first direction, according to an operation of the second driving motor.

Also, a direction of motion of the pressurizing part and a direction of rotation plane of the main gear may be vertical.

The microneedle applicator further includes a touch sensor configured to be electrically connected to the controller and generate an electrical signal reflecting the state of contact with an object, wherein the controller may transmit a driving signal to the drive mechanism when a magnitude of the electrical signal generated by the touch sensor is greater than or equal to a threshold value.

Also, the second drive mechanism includes a lower plate to protect the microneedle patch, and the lower plate is located on a lower part of the microneedle patch and may rotate with the main gear and the pressurizing part when the microneedle patch is mounted on the applicator.

The lower plate includes a pressurizing-opening part, locations of the pressurizing-opening part and the pressurizing part correspond to each other, and when the first drive mechanism is actuated, at least a portion of the pressurized microneedle patch may protrude through the pressurizing-opening part.

According to another embodiment of the present disclosure, a microneedle applicator includes: a patch delivery part configured to place a microneedle patch in a predetermined area; a housing including an accommodating part defined as a space for accommodating the patch delivery part and at least one opening; and a pressurizing part configured to apply a predetermined pressure to the microneedle patch, wherein the pressurizing part moves between a first position and a second position, and when the pressurizing part is at the second position, the pressurizing part comes into contact with the microneedle patch disposed in the predetermined area and applies the predetermined pressure to at least a portion of the microneedle patch, and the microneedle patch to which the predetermined pressure is applied may be delivered directly to the skin through the opening.

The microneedle applicator may further include a strip for securing the applicator to a user's body.

The patch delivery part includes a cartridge; the cartridge contains a plurality of microneedles; and the plurality of microneedles may be used a predetermined number of times for injections.

Also, the microneedle applicator further includes a driving part, wherein the driving part may provide a driving force to at least one of the patch delivery part and the pressurizing part.

The driving part may include at least one or more motor.

Also, the microneedle patch has a preset dose of a drug stored at least a portion of therein; the applicator further comprises a controller; the controller may control at least one of the driving part, the patch delivery part, and the pressurizing part so that a preset dose stored in at least a portion of the microneedle patch may be injected into the user's skin.

The controller may control the pressurizing part to move between the first position and the second position and to apply the preset pressure to the microneedle patch at the second position.

At the second position, at least a portion of the microneedle patch pressurized by a predetermined displacement by the pressurizing part may be exposed through the opening.

At the first position, the pressurizing part does not pressurize the microneedle patch and at least a portion of the microneedle patch may not be exposed.

In addition, the applicator may be offered as a wearable watch.

According to yet another embodiment of the present disclosure, a microneedle patch includes a body in which at least one opening is formed, and a microneedle body which is disposed in the opening and has at least one microneedle formed therein, wherein when an external force is applied in a first direction, the microneedle body moves in the first direction so as to administer a drug in the microneedle to a user's skin.

The microneedle patch further include a connecting part, and when an external force is applied in a first direction on the microneedle body located at a first position, the microneedle body is moved to a second position by the elastic deformation of the connecting part, and the microneedle body moved to the second position may move in a second direction opposite to the first direction.

The microneedle body, which has moved to the second position, may move back to the first position in the second direction.

Hereinafter, the general configuration of a drug delivery device according to an embodiment will be described with reference to FIGS. 1 and 2.

Figure 2:
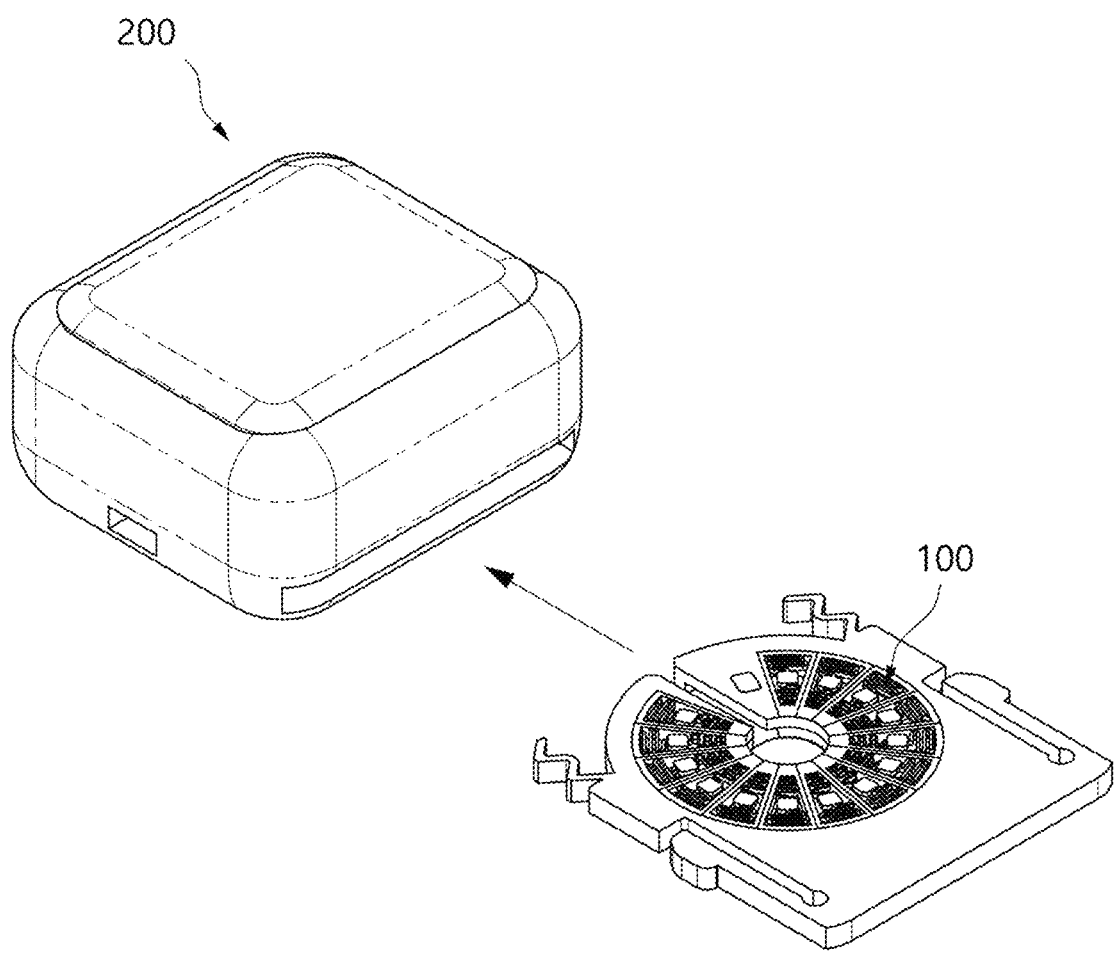
FIG. 2 is a half exploded view illustrating the general configuration of a drug delivery device according to an embodiment.

FIG. 1 illustrates the overall appearance of a drug delivery device according to an embodiment and FIG. 2 is a half exploded view illustrating the general configuration of a drug delivery device according to an embodiment.

A description will be provided with reference to FIGS. 1 and 2.

According to an embodiment of the present disclosure, a drug delivery device 1 capable of supplying a drug to a user may be provided. That is, the drug delivery device 1 according to an embodiment may deliver the drug to the user according to the user's use.

To this end, the drug delivery device according to an embodiment may be mounted on the user's body. In other words, the drug delivery device 1 in the present specification may be implemented in the form of a wearable device. To be provided in the form of a wearable device, all means for attaching the drug delivery device 1 to the user's body, such as bands and strips, may be provided together. The drug delivery device 1 may be mounted on the user's wrist, ankle, arm, leg, and etc., and it will be understood that it may be mounted on any body part suitable for supplying a drug to the user.

Also, the drug delivery device 1 according to an embodiment may include an applicator 200 and a cartridge 100. That is, in the present specification it was expressed as the drug delivery device 1 including the applicator 200 and the cartridge 1000, but this is only for convenience of description and it should be understood that the applicator 200 and the drug delivery device 1 may be used interchangeably.

The applicator 200 may accommodate the microneedle patch 100. That is, a microneedle patch 100 may be mounted in the applicator 200.

When the microneedle patch 100 is mounted in the applicator 200, the applicator 200 may deliver the drug stored in the microneedle patch 100 to the inside of the user's body.

Hereinafter, with reference to the drawings, the microneedle patch according to the embodiment will be described first.

Figure 3:
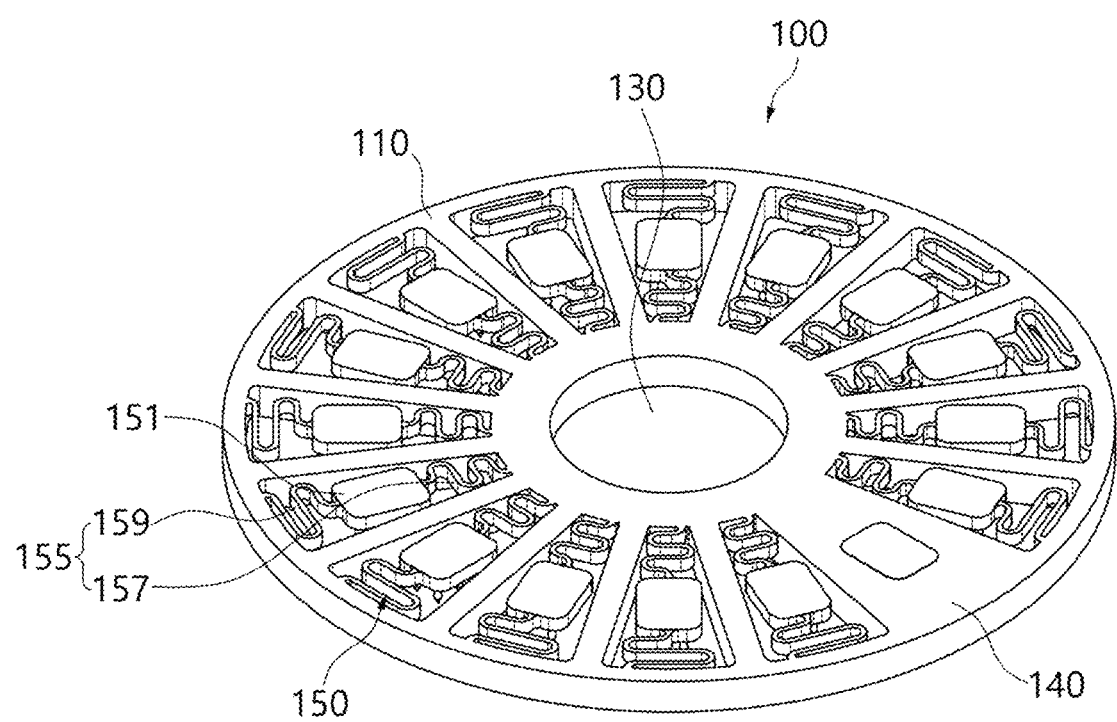
FIG. 3 is a front stereoscopic view of a microneedle patch according to the first embodiment.
Figure 4:
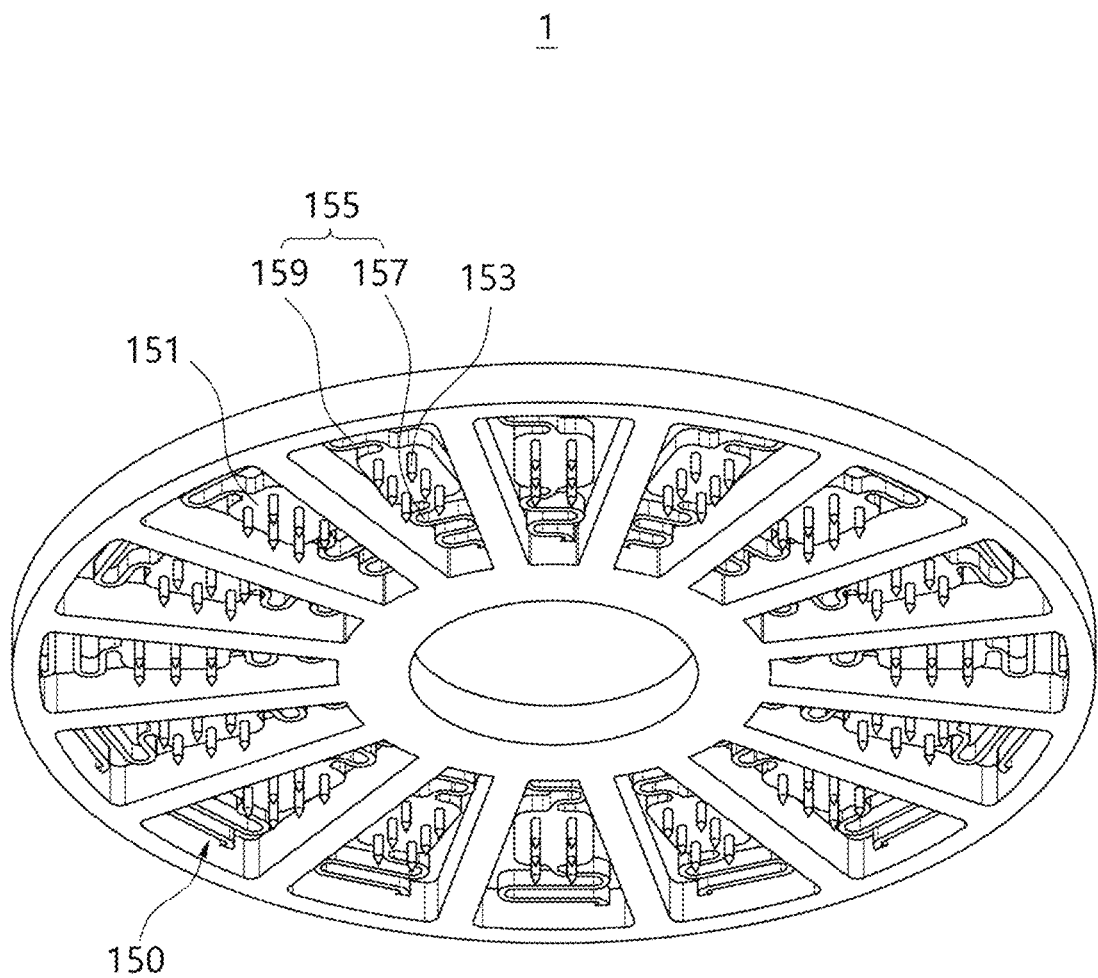
FIG. 4 is a rear stereoscopic view of a microneedle patch according to the first embodiment.
Figure 5:
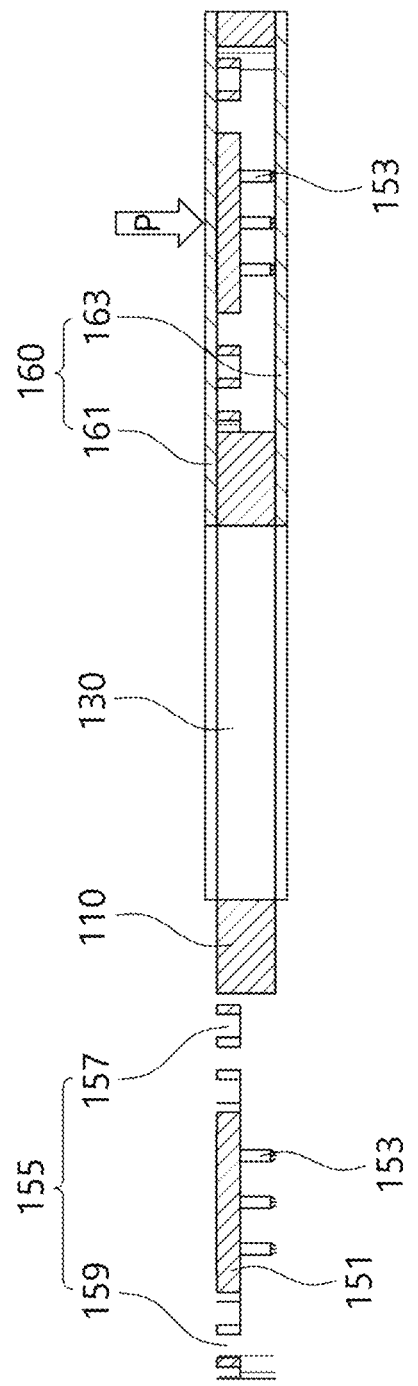
FIG. 5 is a cross-sectional view of a microneedle patch according to the first embodiment.
Figure 6:
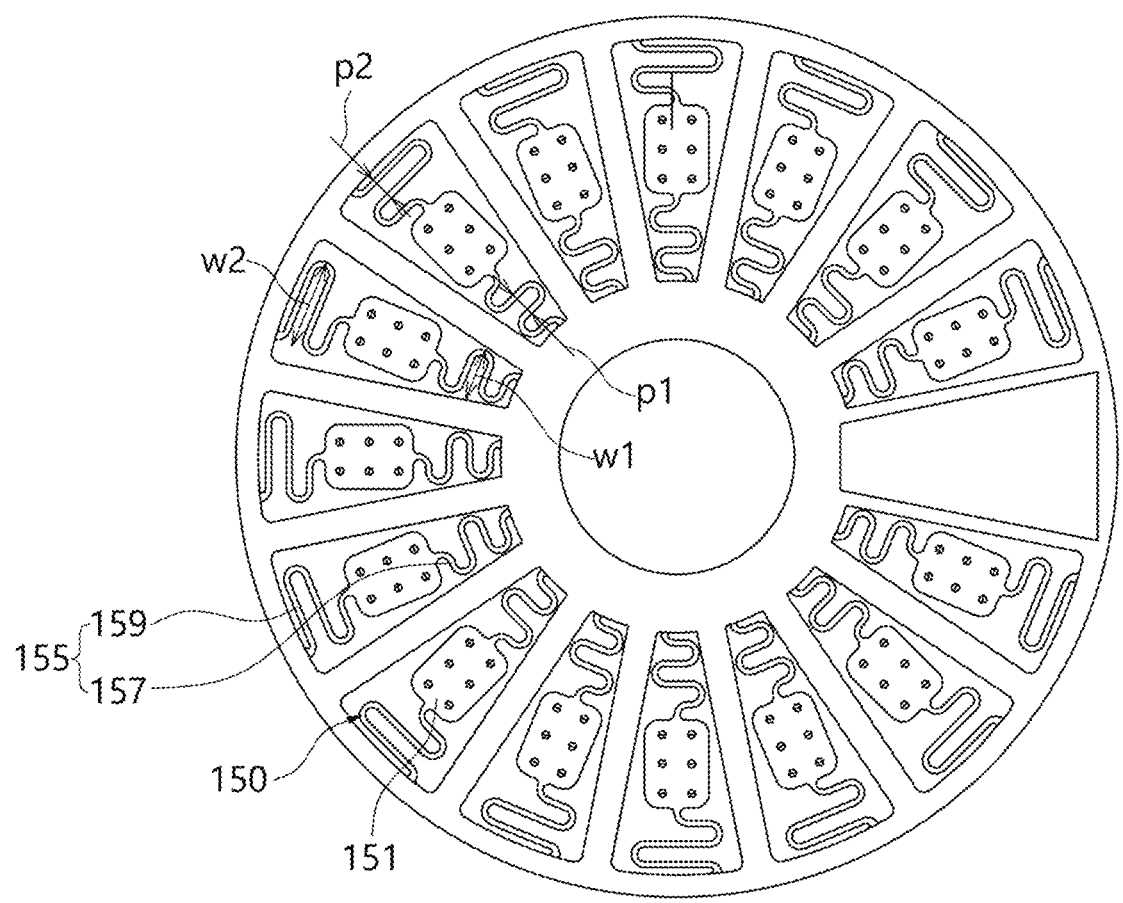
FIG. 6 is a bottom view of a microneedle patch according to the first embodiment.

FIG. 3 is a front stereoscopic view of a microneedle patch according to the first embodiment, FIG. 4 is a rear stereoscopic view of a microneedle patch according to the first embodiment, FIG. 5 is a cross-sectional view of a microneedle patch according to the first embodiment, and FIG. 6 is a bottom view of a microneedle patch according to the first embodiment.

Referring to FIGS. 3 to 6, the microneedle patch 100 according to the first embodiment may include a body 110, an opening 120, a shaft connecting part 130, an auxiliary area 140, and a microneedle structure body 150.

The microneedle patch 100 according to the first embodiment may be inserted into a watch-type wearable device. When inserted into a wearable device, the microneedle patch 100 may be operated in combination with the driving structure implemented in the wearable device. For example, the microneedle patch 100 may be rotated by the wearable device, and a portion may be moved in the first direction by being pressurized by the driving structure of the microneedle patch 100.

In addition, the microneedle patch 100 is fixed to the wearable device, and a portion of the micro patch 100 may be moved in the first direction when rotated and pressurized by the driving structure of the microneedle patch 100.

The microneedle patch 100 may have a replaceable structure. When the microneedle patch 100 has a replaceable structure, the microneedle patch 100 may be combined with other hardware structures to form a cartridge assembly. In this case, the microneedle patch 100 may be mounted on the cartridge assembly and inserted into the wearable device. The cartridge assembly may be replaced when the injection of the drug attached to the microneedle patch 100 is completed or according to other needs.

The body 110 may serve as a frame of the microneedle patch 100. The body 110 may be a plate shape. The body 110 may be a circular plate shape. That is, the body 110 may be a thin disk shape.

A plurality of openings 120 and a shaft connecting part 130 may be formed in the body 110. The plurality of openings 120 may be formed to pass through the body 110. The plurality of openings 120 may be arranged in a sectoral shape with respect to the center of the body 110. The plurality of openings 120 may be located at a predetermined distance from the adjacent openings 120. Alternatively, although not shown, the plurality of openings 120 may be arranged in various shapes such as a circle.

The opening 120 may have a different area size depending on a distance from the center of the body 110. For example, an area of a region adjacent to the center of the body 110 among the openings 120 may be smaller than an area of a region spaced apart from the center 110 of the body. The opening 120 may be formed to have a larger area as the distance from the center of the body 110 increases.

The shaft connecting part 130 may be formed to pass through the body 110. The shaft connecting part 130 may be formed in the center of the body 110. The shaft connecting part 130 may be formed in a circular shape based on the center of the body 110. That is, the center of the shaft connecting part 130 may be the same as that of the body 110. The outer diameter of the shaft connecting part 130 may be smaller than that of the body 110. The plurality of openings 120 may be formed between the outer diameter of the shaft connecting part 130 and the outer diameter of the body 110.

An external structure for fixing or rotating the microneedle patch 100 may be inserted into the shaft connecting part 130. The external structure may be a partial structure of the wearable device, or may be a partial structure of the cartridge assembly. The external structure may rotate the microneedle patch 100 by an operating structure of the wearable device. On the other hand, the microneedle patch 100 may be fixed to the wearable device by a structure coupled to the body 110.

An auxiliary region 140 may be formed in the body 110. The auxiliary region 140 may be a region in which the opening 120 is not formed. The auxiliary region 140 may be an unopened region of the body 110. The plurality of openings 120 are located at regular intervals, and the opening 120 may not be formed in an area where one opening 120 can be located, and an area in which the opening 120 is not formed may be defined as the auxiliary region 140. The auxiliary region 140 may serve as a door blocking the cartridge assembly from the outside when the wearable device is in a standby state rather than a drug injection state. The auxiliary region 140 may serve to block the internal structure of the wearable device from the outside in the standby state. By the auxiliary region 140, the cartridge assembly and the internal structure of the wearable device may be protected from external moisture or foreign substances.

The microneedle structure body 150 may be located in the opening 120. The microneedle structure body 150 may be moved when an external force is applied. The microneedle structure body 150 may move in the same direction with the external force when the external force is applied, then return to the original position again. The microneedle structure body 150 may move in the same direction with the external force when the external force is applied, and when the external force is released, may return to the original position again.

For example, when the external force is applied in the first direction while the microneedle structure body 150 is positioned at the first position, the microneedle structure body 150 may move in the first direction to the second position, then return to the first position by moving in the second direction opposite to the first direction. The microneedle structure body 150 moved to the second position may move in the second direction when the external force is released, and return to the first position. The first position may be an initial position of the microneedle structure body 150.

Since the microneedle structure body 150 has an elastic structure, it can move in the first direction by the external force, and can move again in the second direction when the external force is released.

The external force may be applied to the microneedle structure body 150 by the operating structure of the wearable device, or the external force may be applied to the microneedle structure body 150 by the operating structure of the cartridge assembly. The external force may be transmitted to the microneedle structure body 150 by a power source located inside the wearable device.

The microneedle structure body 150 may include a microneedle body 151 and a connecting part 155.

The microneedle body 151 may be formed in a plate shape having both sides.

The microneedle body 151 may include a plurality of microneedles 153. The plurality of microneedles 153 may be formed on one surface of the microneedle body 151. The plurality of microneedles 153 may be formed to protrude from the microneedle body 150 in the first direction.

The plurality of microneedles 153 may serve to deliver drugs to the user's skin. The plurality of microneedles 153 may be composed of at least one type of a coated type, a hollow type, a dissolving type, and a swelling type.

When the microneedle 153 is a coated type, the outside of the microneedle 153 is coated with the drug and when the microneedle is injected into the user's skin, the drug coated on the microneedle 153 can be delivered to the user's skin.

When the microneedle 153 is a hollow type, a hollow is formed in the microneedle 153 and when the microneedle is injected into the user's skin, the drug that was injected in the hollow can be delivered to the user's skin.

When the microneedle 153 is a dissolving type, the microneedle 153 itself is formed of a drug and when the microneedle is injected into the user's skin, the microneedle 153 itself is delivered to the user, and then the microneedle is dissolved in the user's skin so that the drug can be delivered to the user's skin.

When the microneedle 153 is a swelling type, a swellable material containing a drug is coated on the outside of the microneedle 153, and when the microneedle is injected into the user's skin, the coated material swells so that the drug can be structurally bonded to the user's skin and delivered to the user.

An external force may be applied to the other surface of the microneedle body 151. When the external force is applied to the other surface of the microneedle body 151 in the first direction, a plurality of microneedles 153 formed on one surface of the microneedle body 151 may move in the direction of the user's skin to deliver the drug to the user's skin.

The connecting part 155 may connect the microneedle body 151 and the body 110. The connecting part 155 may be formed in a structure having elasticity. The connecting part 155 may be formed in a structure that can be elastically deformed. However, the elastic deformation may be a temporary deformation.

When an external force is applied to the microneedle body 151 in the first direction, the connecting part 155 may be elastically deformed so that the microneedle body 151 moves in the first direction while the microneedle body 151 maintains the connection with the body 110. Also, when the external force is released, the microneedle body 151 may be moved in the second direction by the elasticity of the connecting part 155.

The plurality of microneedle bodies 151 included in the microneedle patch 100 are rotated by the elasticity of the connecting part 155 to deliver the drug to the skin once per rotation. As such, the microneedle patch 100 has the effect of performing drug delivery multiple times.

The connecting part 155 may include a first connecting part 157 and a second connecting part 159.

The first connecting part 157 may be located in an area adjacent to the shaft connecting part 130. The second connecting part 159 may be located in an area spaced apart from the shaft connecting part 130. The first connecting part 157 may be located in a region adjacent to the center of the body 110, and the second connecting part 159 may be located in an area adjacent to the outer diameter of the body 110.

The first connecting part 157 may connect one side of the microneedle body 151 and the body 110, and the second connecting part 159 may connect the other side of the microneedle body 151 to the body 110.

The first connecting part 157 and the second connecting part 159 may be formed in a structure having a curved shape. The first connecting part 157 and the second connecting part 159 may have elasticity by being formed in a structure having a curved shape. The first connecting part 157 and the second connecting part 159 may be designed as a structure having different elastic forces. The first connecting part 157 and the second connecting part 159 may be formed in a structure having elasticity to move in the first direction when an external force is applied to the microneedle body 151 in the first direction. That is, the first connecting part 157 and the second connecting part 159 may be designed in a structure having elasticity so that it can move to the second position in a state parallel to the upper surface of the body 110 when an external force is applied in the first direction.

The first connecting part 157 and the second connecting part 159 may be formed in a spring structure.

The first connecting part 157 and the second connecting part 159 each may be formed in a curved structure having a width and a pitch. The first connecting part 157 may have a structure having a width and a pitch different from that of the second connection part 159.

The first connecting part 157 may have a first width w1 and a first pitch p1. The first width w1 may be defined as a distance between the regions of the first connecting part 157 that is farthest apart based on an imaginary line connecting the center of the microneedle body 151 to the center of the body 110. The first pitch p1 may be defined as an distance between adjacent regions within the first connection part 157. That is, the first pitch p1 may be defined as a minimum distance between adjacent regions within the first connecting part 157 based on an imaginary line connecting the center of the microneedle body 151 and the center of the body 110.

The second connecting part 159 may have a second width w2 and a second pitch p2. The second width w2 and the second pitch p2 may also be defined as a meaning corresponding to the first width w1 and the first pitch w2 of the first connection part 157.

The first width w1 may be smaller than the second width w2. The first pitch p1 may be greater than or equal to the second pitch p2.

In addition, the first connecting part 157 and the second connecting part 159 may have a curved section and a straight section. In this case, the width of the first connecting part 157 and the second connecting part 159 may be defined as an interval between a straight line connecting inflection points of one curved section and a straight line connecting inflection points of the other curved section. The pitch of the first connecting part 157 and the second connecting part 159 may be defined as an interval between the straight sections.

The microneedle body 151, the first connecting part 157, and the second connecting part 159 may be integrally formed. The microneedle body 151, the first connecting part 157, and the second connecting part 159 may have the same thickness. Alternatively, although not shown, the thickness of the microneedle body 151 may be greater or smaller than the thickness of the first connecting part 157 and the second connecting part 159.

The body 110 and the microneedle structure body 150 may be integrally formed. Also, the body 110, the microneedle structure body 150, and the microneedle 153 may be integrally formed.

A protective film 160 may be formed on at least one surface of the body 110. The protective film 160 may serve to protect the microneedle body 151 from the outside.

The protective film 160 may include an upper protective film 161 and a lower protective film 163. The upper protective film 161 may be formed on the upper surface of the body 110, and the lower protective film 163 may be formed on the lower surface of the body 110.

The protective film 160 may be made of a material including metal. The protective film 160 may be made of aluminum. Also, the protective film 160 may be made of plastics.

The protective film 160 may be damaged by the microneedle 151 when the microneedle structure body 150 is pressurized by the external structure, so that the microneedle 151 may deliver a drug to the user's skin.

Alternatively, when drug injection from a specific microneedle structure body 150 among a plurality of microneedle structure bodies 150 is scheduled, the protective film 160 in the area corresponding to the specific microneedle structure 150 may be damaged or removed in advance just before pressurization by the external structure, so that drug injection by the microneedle 151 can be performed more smoothly. In this case, a portion of the protective film 160 may be damaged, moved, or removed by some structures of the cartridge assembly or the wearable device.

Figure 7:
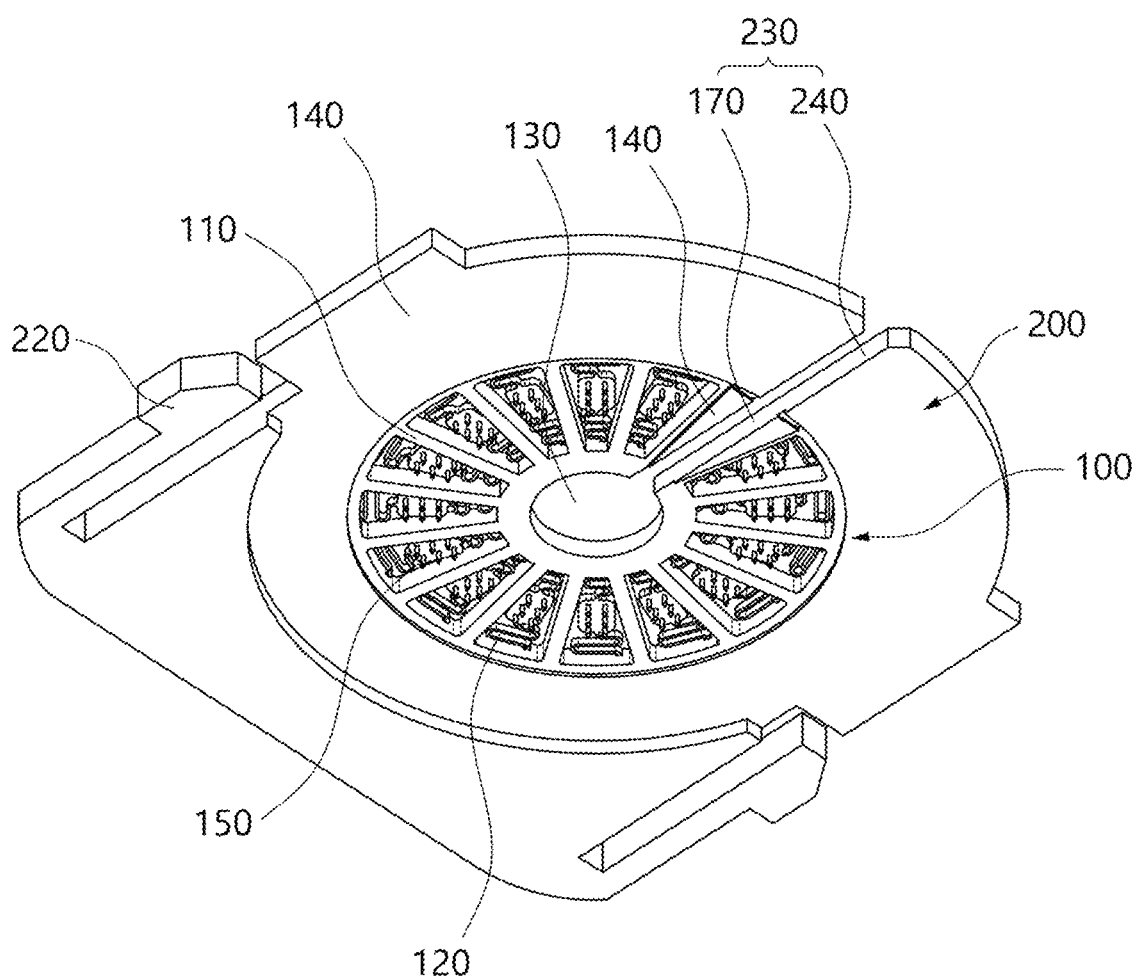
FIG. 7 is a bottom perspective view illustrating a patch assembly according to the second embodiment.

FIG. 7 is a bottom perspective view illustrating a patch assembly according to the second embodiment.

The patch assembly according to a second embodiment is provided in a form in which a microneedle patch is mounted on a patch carrier without a separate cartridge housing. Therefore, in the description of the patch assembly according to a second embodiment, the same reference numerals are assigned to the descriptions common to those of a first embodiment, and detailed descriptions thereof are omitted.

Referring to FIG. 7, the patch assembly according to the second embodiment includes a microneedle patch 100 and a patch carrier 200.

The microneedle patch 100 may be mounted on the patch carrier 200. The microneedle patch 100 may be rotatably mounted on the patch carrier 200.

The microneedle patch 100 may include a body 110, a plurality of openings 120, a shaft connecting part 130, an auxiliary region 140, and a microneedle structure body 150.

The patch carrier 200 may include a carrier body 210 and a coupling structure 220.

The carrier body 210 constitutes a frame of the patch carrier 200. A seating part may be formed on the carrier body 210, and the microneedle patch 100 may be rotatably mounted to the seating part.

The coupling structure 220 may be formed in a portion of the carrier body 210. The coupling structure 220 may have a shape protruding to the outside. The coupling structure 220 may serve to fix the patch carrier 200 to the wearable device when the patch carrier 200 is mounted on the wearable device.

A through groove 230 may be formed in the patch assembly. The through groove 230 may serve as a path through which a power transmission structure among the internal structures of the wearable device moves from the outside of the patch assembly to the shaft connecting part 130. That is, when the patch assembly is inserted into the wearable device, the through groove 230 may be a moving path for the power transmission structure, which should be located in the shaft connecting part 130 when the installation is complete, to move to the shaft connecting part 130 without structural interference.

The through groove 230 may include a patch through groove 170 and a carrier through groove 240. The patch through groove 170 may be formed to extend from the shaft connecting part 130 to the outer diameter of the body 110. The patch through groove 170 may be formed in the auxiliary region 140.

The carrier through groove 240 may be formed to pass through the seating part and the carrier body 210. The patch through groove 170 and the carrier through groove 240 may be formed in corresponding regions.

The patch assembly according to the second embodiment is provided in a form in which a microneedle patch is mounted on a patch carrier without a separate cartridge housing, so that it can be implemented with a simple structure, thereby reducing the manufacturing cost. In addition, since the patch assembly has the through groove 230, the power transmission structure of the wearable device can be positioned with the shaft connecting part 130 without structural interference, thereby omitting a separate movement mechanism.

Figure 8:
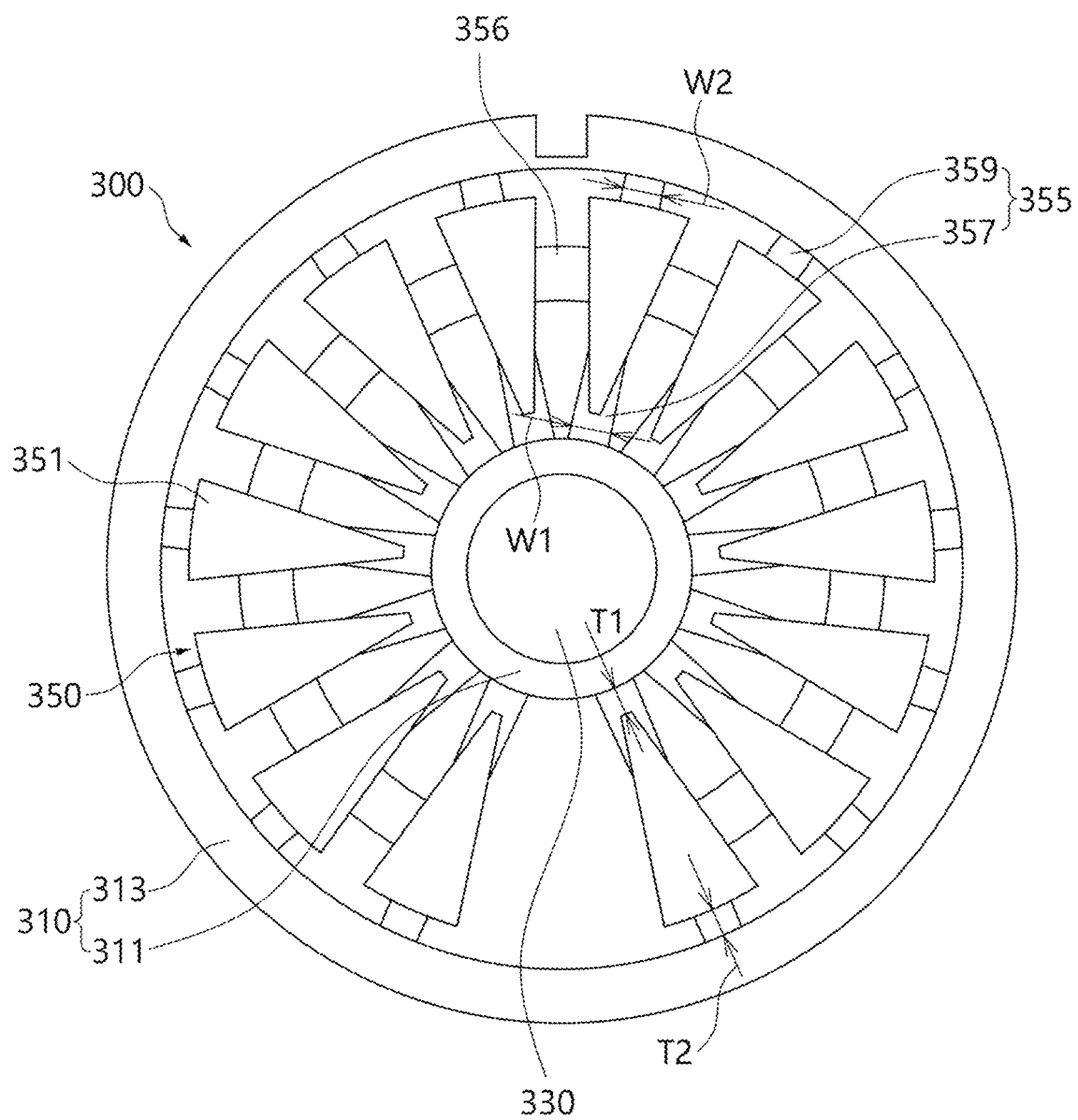
FIG. 8 is a top view illustrating a microneedle patch according to the third embodiment.

FIG. 8 is a top view illustrating a microneedle patch according to the third embodiment.

The microneedle patch according to the third embodiment is different from the first embodiment in the shape of the connecting part, the microneedle body, and the shape of the body corresponding thereto, and the rest of the configuration is the same. Therefore, in the description of the third embodiment, the same reference numerals are assigned to the components common to the first embodiment, and detailed descriptions thereof are omitted.

Referring to FIG. 8, the microneedle patch 300 according to the third embodiment may include a body 310, a shaft connecting part 330, and a microneedle structure body 350.

The body 310 may include a first body 311 and a second body 313. The first body 311 and the second body 313 may have a circular band shape. The first body 311 and the second body 313 may have a circular band shape having the same center. The first body 311 and the second body 313 may have different radii. The first body 311 may have a smaller radius than that of the second body 313. The second body 313 may be formed to surround the first body 311. The first body 311 and the second body 313 may be formed to be spaced apart from each other. The first body 311 and the second body 313 may be spaced apart from each other to form an opening.

The microneedle structure body 350 may be located in an opening between the first body 311 and the second body 313. At least one microneedle structure 350 may be positioned in the opening.

The microneedle structure 350 may be connected to the first body 311 and the second body 313.

The microneedle structure 350 may include a microneedle body 351, a connecting part 355, and an annular connecting part 356.

A microneedle may be formed in the microneedle body 351.

The microneedle body 351 may be formed in a sectoral shape. In the drawings, the microneedle body 351 has been described as having a sectoral shape, but is not limited thereto.

The widths of one end and the other end of the microneedle body 351 may be different. One end of the microneedle body 351 may be adjacent to the first body 311, and the other end of the microneedle body 351 may be adjacent to the second body 313. The width of one end of the microneedle body 351 may be smaller than the width of the other end.

The microneedle body 351 may be connected to the main body 310 by the connecting part 355. The connecting part 355 may be arranged toward the center of the circle.

The connecting part 355 may include a first connecting part 357 and a second connecting part 359.

The first connecting part 357 may be positioned between the microneedle body 351 and the first body 311. The first connecting part 357 may connect the first body 311 and the microneedle body 351. The first connecting part 357 may have a first width W1 and a first thickness T1.

The second connecting part 359 may be positioned between the microneedle body 351 and the second body 313. The second connecting part 359 may connect the second body 313 and the microneedle body 351. The second connecting part 359 may have a second width W2 and a second thickness T2.

The first width W1 may be different from the second width W2, and the first thickness T1 may be different from the second thickness T2.

The annular connecting part 356 may connect the adjacent microneedle body 351. The annular connecting part 356 may connect the side surfaces of the adjacent microneedle body 351. The annular connecting part 356 may be formed in a shape corresponding to the main body 310. A plurality of annular connecting parts 356 may be formed to be spaced apart from each other along a circular band shape. The annular connecting part 356 may be disposed along a circle having the same center as the first body 311.

The connecting part 355 and the annular connecting part 356 may be physically connected in a state formed separately from the microneedle body 351, and at least one of the connecting part 355 and the annular connecting part 356 may be integrally formed with the microneedle body 351.

The connecting part 355 and the annular connecting part 356 may have elasticity. The connecting part 355 may have elasticity in the center direction of the body 310. The annular connecting part 356 may have the same center as the body 310, and may have elasticity in the circumferential direction of a circle in which the annular connecting part 356 is located.

Because the connecting part 355 and the annular connecting part 356 have elasticity, when an external force is applied to the microneedle body 351 in the first direction, the microneedle body 351 may be moved to the second position in a state parallel to the upper surface of the body 310. After moving to the second position, the microneedle body 351 may be moved back to the first position.

Figure 9:
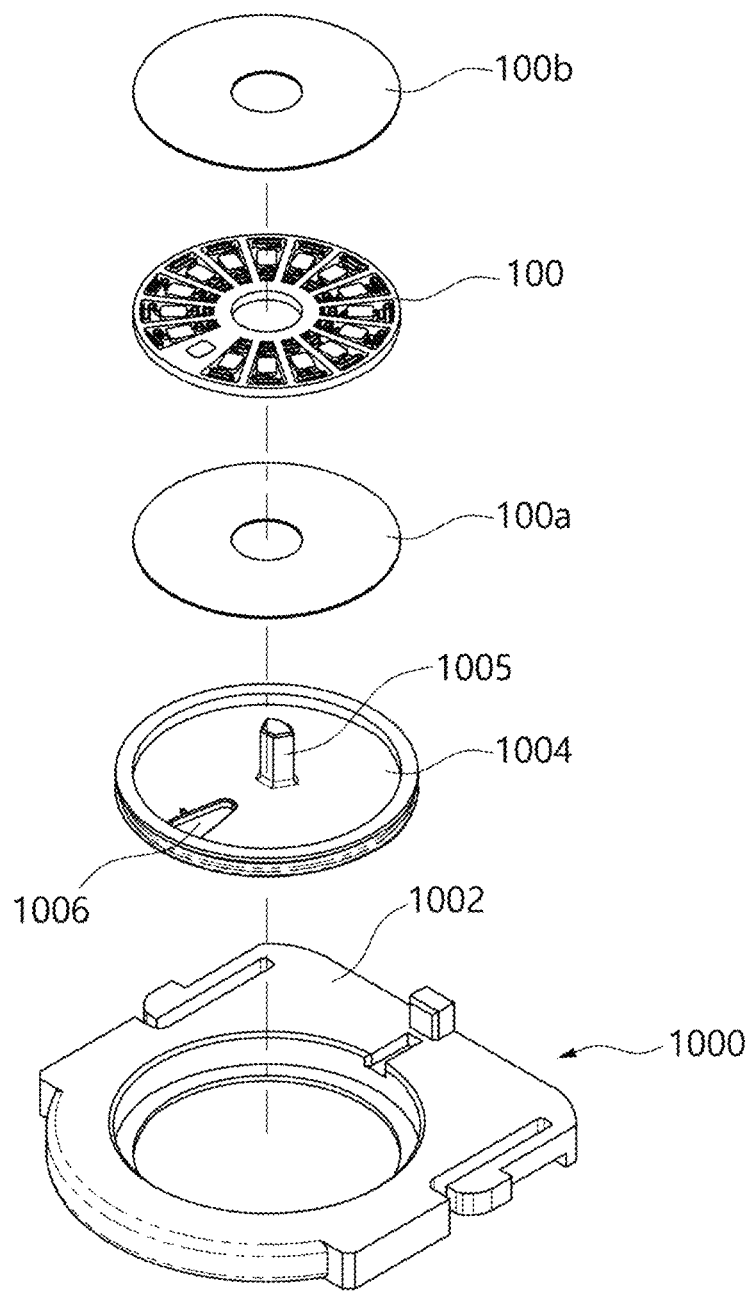
FIG. 9 illustrates a cartridge according to an embodiment.

FIG. 9 illustrates a cartridge according to an embodiment.

Referring to FIG. 9, the microneedle patch 100 may be provided through the cartridge 1000. That is, the microneedle patch 100 may be mounted on the applicator 200 (see FIG. 2) while being mounted or accommodated in the cartridge 1000.

According to an embodiment, the cartridge 1000 may be manufactured together with the microneedle patch 100 and used once. According to another embodiment, the cartridge 1000 may be implemented as a part of the applicator 200 (see FIG. 10) to enable reuse.

In the following description, the cartridge 1000 will be mainly described when implemented as a part of the applicator 200 (see FIG. 10), but it should be noted in advance that this is only for convenience of description.

The cartridge 1000 according to an embodiment may include a body portion 1002 and a flat plate portion 1004. Here, the body portion 1002 may be accommodated in an accommodating part formed in the housing 201 (see FIG. 10) of the applicator 200 (see FIG. 10), as will be described later.

In addition, the flat plate portion 1004 may have a flat plate opening 1006 through which the pressurizing part or the rack gear can pass, as will be described later.

Also, the flat plate portion 1004 may be mounted on the body portion 1002. The flat plate portion 1004 may be inserted into the applicator 200 (see FIG. 10) while being mounted on the body portion 1002. When the flat plate portion 1004 is inserted into the applicator 200 (see FIG. 10), a fixing portion 1005 formed on the flat plate portion 1004 may be operatively coupled to the drive mechanism 210 (see FIG. 10), as will be described later. When the fixing portion 1005 is operatively coupled to the drive mechanism 210 (see FIG. 10), the flat plate portion 1002 may rotate according to the driving of the drive mechanism 210 (see FIG. 10).

In addition, the cartridge 1000 performs a function of placing the microneedle patch 100 (see FIG. 3) in a predetermined area. The microneedle patch 100 (see FIG. 3), generally a microneedle 153 (see FIGS. 3 to 7), is disposed on each microneedle body 151 (see FIG. 3), and since the microneedle included in each microneedle body stores a preset dose of a drug, it is important that the microneedle patch be placed at a predetermined location inside the applicator when injecting into the user through the applicator. To describe this from another point of view, the cartridge 1000 may be expressed as performing a function of delivering a patch to an appropriate location, and the cartridge 1000 may be expressed as a patch delivery unit.

When the cartridge 1000 places the microneedle patch 100 at a predetermined location inside the applicator 200, the applicator 200 may inject a predetermined dose to the user through the drive mechanism 210.

Interaction between the cartridge 1000 and the applicator 200 will be described later in detail.

In addition, since an upper protective film 100a and a lower protective film 100b shown in the drawings are the same as the above-described upper protective film 161 (see FIG. 5) and the lower protective film 163 (see FIG. 5), a detailed description thereof will be omitted.

In the above, the micro-needle patch and the cartridge accommodating the micro-needle patch according to various embodiments were described. Hereinafter, an applicator for applying a microneedle patch according to an embodiment will be described.

Figure 10:
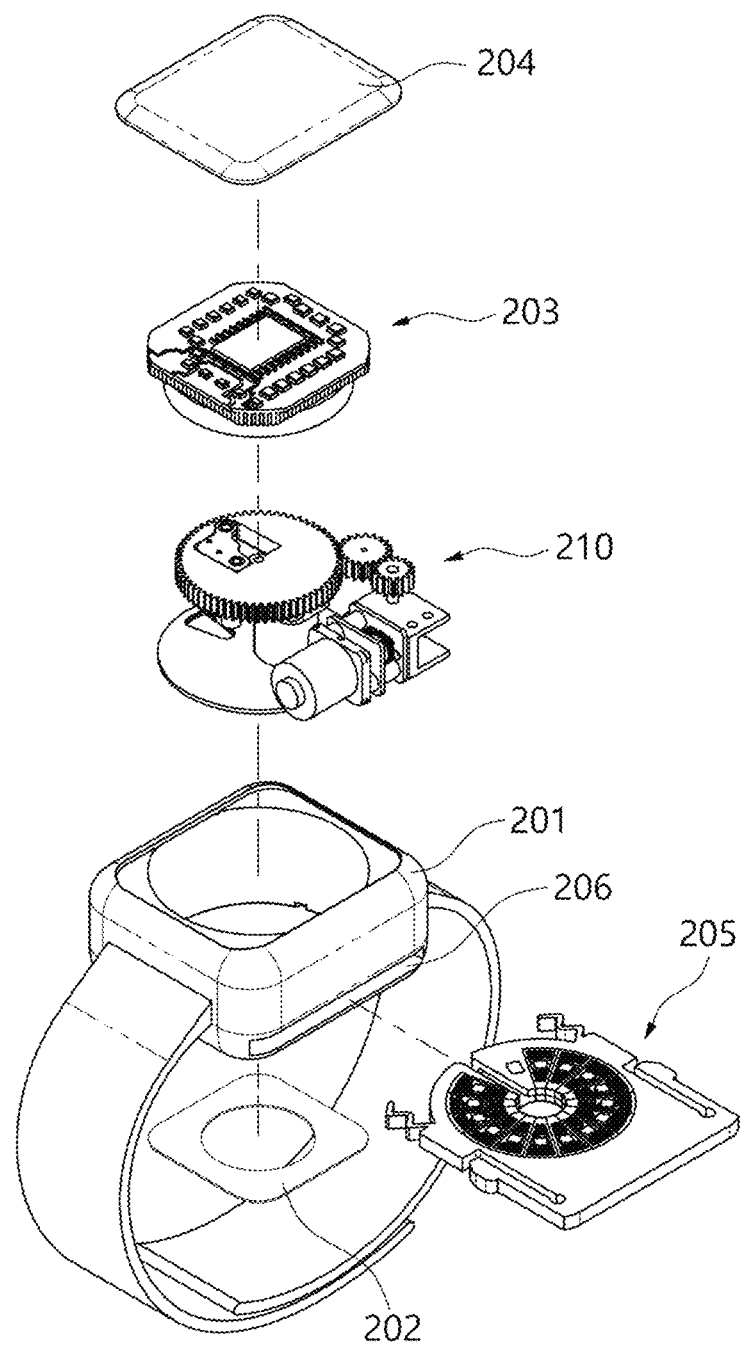
FIG. 10 is a half exploded view illustrating the general configuration of an applicator according to an embodiment.

FIG. 10 is a half exploded view illustrating the general configuration of an applicator according to an embodiment.

Referring to FIG. 10, the applicator 200 according to an embodiment may include a housing 201, a drive mechanism (or drive unit) 210, a PCB 203, and a cartridge 205.

First, the housing 201 serves to protect the components inside the applicator 200, and for this purpose, it is formed to surround the outside of the applicator 200. The shape of the housing 201 may vary according to a design change.

The housing 201 may include an accommodating part 206 for accommodating the cartridge 205 as described above. The accommodating part 206 may be formed to correspond to the shape of the cartridge 205. The accommodating part 206 may be formed in the form of an opening in the housing 201, and an accommodating space corresponding to the shape of the cartridge 205 may be formed inside the housing 201.

Also, according to an embodiment, the housing 201 may have an open bottom shape, and in this case, the housing 201 may include a lower cover 202. The lower cover 202 may be mounted on the open bottom of the housing 201. The lower cover 202 may function to support the cartridge 205. As will be described later, the lower cover 202 may include an opening so that, when the microneedle patch 100 (see FIG. 3) is pressurized according to the operation of the drive mechanism 210, the microneedle patch 100 (see FIG. 3) comes in contact with the user's body.

The drive mechanism 210 may be mounted inside the housing 201. The drive mechanism 210 may include at least one or more motors and gears. The drive mechanism 210 provides power for the applicator 200 to pressurize the microneedle patch 100 (see FIG. 3). A detailed description of the drive mechanism 210 will be described in detail with reference to FIGS. 11 to 17.

The PCB 203 is electrically connected to the drive mechanism 210 and may be mounted inside the housing 201. The PCB 203 may include an MCU, and the drive mechanism 210 may operate as a driving signal generated by the MCU is transmitted to the drive mechanism 210. Also, the overall operation of the applicator 200 can be controlled according to the design of an electrical circuit formed on the PCB.

In addition, the applicator 200 includes a power source for receiving power. The power source may be electrically connected to the PCB 203. The powered PCB may generate a driving signal and transmit it to the drive mechanism 210, and the drive mechanism 210 that receives the driving signal operates so that the applicator 200 pressurizes the microneedle patch 100 (see FIG. 3) to provide a drug to the user.

The applicator 200 according to an embodiment may include a display module 204. Various indications may be provided to the user through the display module 204.

Hereinafter, the operation of the drive mechanism 210 will be described with reference to the drawings.

Figure 11:
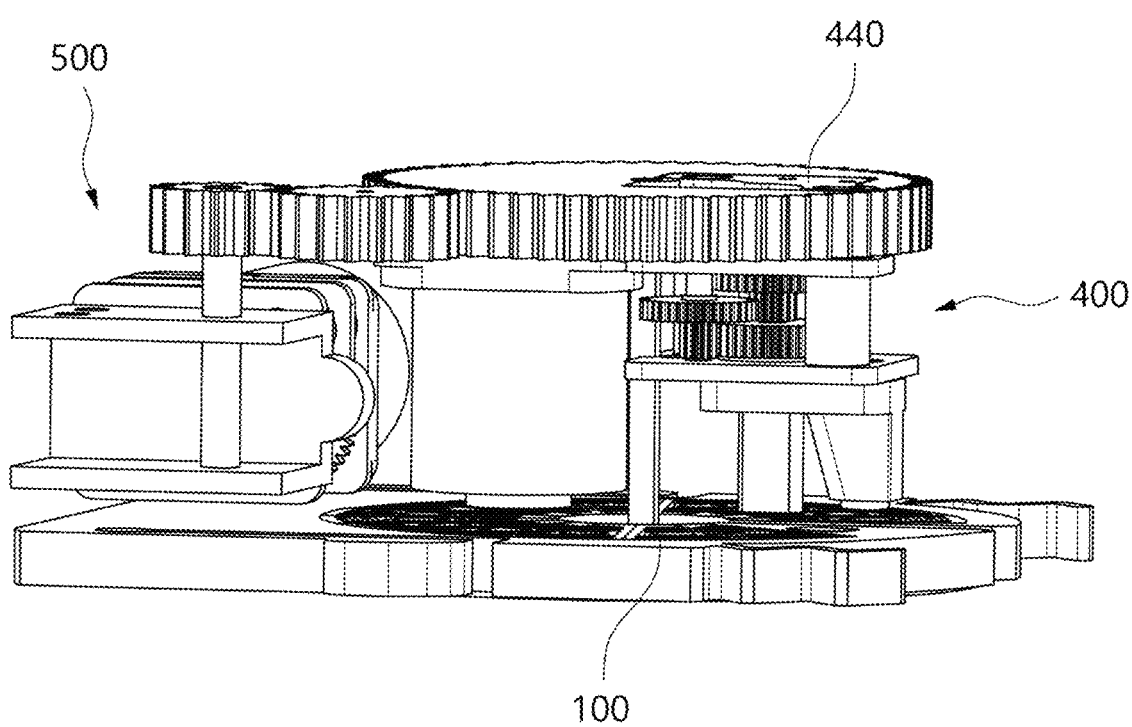
FIG. 11 is a schematic diagram illustrating a drive mechanism according to an embodiment.

FIG. 11 is a schematic diagram illustrating a drive mechanism according to an embodiment.

According to an embodiment, the drive mechanism 210 may pressurize at least a portion of the microneedle patch 100 (see FIG. 3).

Referring to FIG. 11, the drive mechanism 210 may include a first drive mechanism 400 and a second drive mechanism 500. Here, the first drive mechanism 400 and the second drive mechanism 500 may be operatively connected through the connecting unit 440. Also, the first drive mechanism 400 and the second drive mechanism 500 may be operatively connected through a shaft 450 (see FIG. 12)

First, the first drive mechanism 400 according to an embodiment may perform an operation of pressurizing at least a portion of the microneedle patch 100. The second drive mechanism 500 may perform an operation of changing the posture or position of the first drive mechanism 400 so that the first drive mechanism 400 can pressurize an appropriate point of the microneedle patch 100.

Specifically, when the second drive mechanism 500 operates, the first drive mechanism 400 may move in response to the operation of the second drive mechanism 500. When the first drive mechanism 400 has a posture for pressurizing the microneedle patch 100 by moving in response to the operation of the second drive mechanism 500, the first drive mechanism 400 is operated to pressurize the microneedle patch 100.

Hereinafter, a specific configuration of the first drive mechanism 400 will be described with reference to the drawings.

Figure 12:
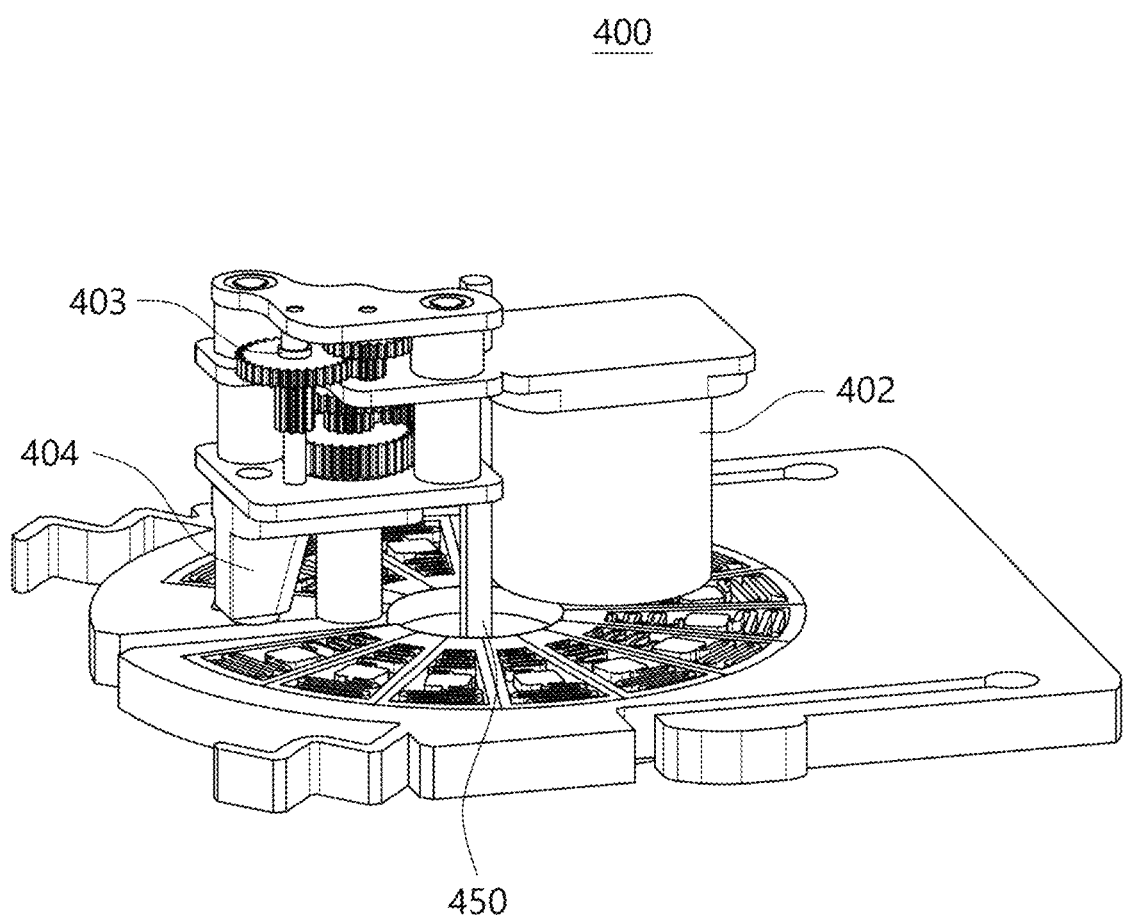
FIG. 12 illustrates a configuration of the first drive mechanism according to an embodiment.

FIG. 12 illustrates a configuration of the first drive mechanism according to an embodiment.

Referring to FIG. 12, the first drive mechanism 400 according to an embodiment may include a first driving motor 402, at least one first connecting gear 403, and a pressurizing part 404.

The first driving motor 402 may be engaged with at least one or more first connecting gears 403, and at least one or more of the first connecting gears 403 may be operatively connected to the pressurizing part 404. Here, the gear structure of the at least one or more first connecting gears 403 may be variously changed in design to achieve the object of the present disclosure, and it will be apparent that such modifications are also incorporated within the spirit of the present disclosure.

The first driving motor 402 may operate by receiving a driving signal and power from the above-described PCB.

When the first driving motor 402 operates, at least one or more first connecting gears 403 may be engaged with the first driving motor 402 to operate. When at least one first connecting gear 403 that has received the power of the first driving motor 402 operates, the pressurizing part 404 operatively connected with the first connecting gear 403 may operate.

The pressurizing part 404 may pressurize at least a portion of the microneedle patch 100 by moving translationally along an axis perpendicular to the surface of the microneedle patch 100. That is, by operating the first drive mechanism 400 according to the driving signal received from the PCB, the pressurizing part 404 can pressurize at least a portion of the microneedle patch 100. Here, the pressurizing part 404 may move by a predetermined displacement according to the operation of the first drive mechanism 400. In other words, it may be expressed that the pressurizing part 404 can move from the first position to the second position according to the operation of the first drive mechanism 400. Also, the pressurizing part 404 applies a predetermined pressure to at least a partial region (e.g., the microneedle body) of the microneedle patch 100 (see FIG. 3) by moving a predetermined displacement or moving between predetermined positions.

In addition, the first drive mechanism 400 may be connected to the second drive mechanism 500 through the shaft 450 and the connecting part 440. As will be described later, the shaft 450, which is the axis of rotation of the second drive mechanism 500, and the first drive mechanism 400 are connected, so that the first drive mechanism 400 rotates as a whole relative to the shaft 450 according to the operation of the second drive mechanism 500, and the pressurizing part 404 may pressurize the microneedle patch 100 at a suitable location.

Hereinafter, an operation of the second drive mechanism 500 will be described with reference to the drawings.

Figure 13:
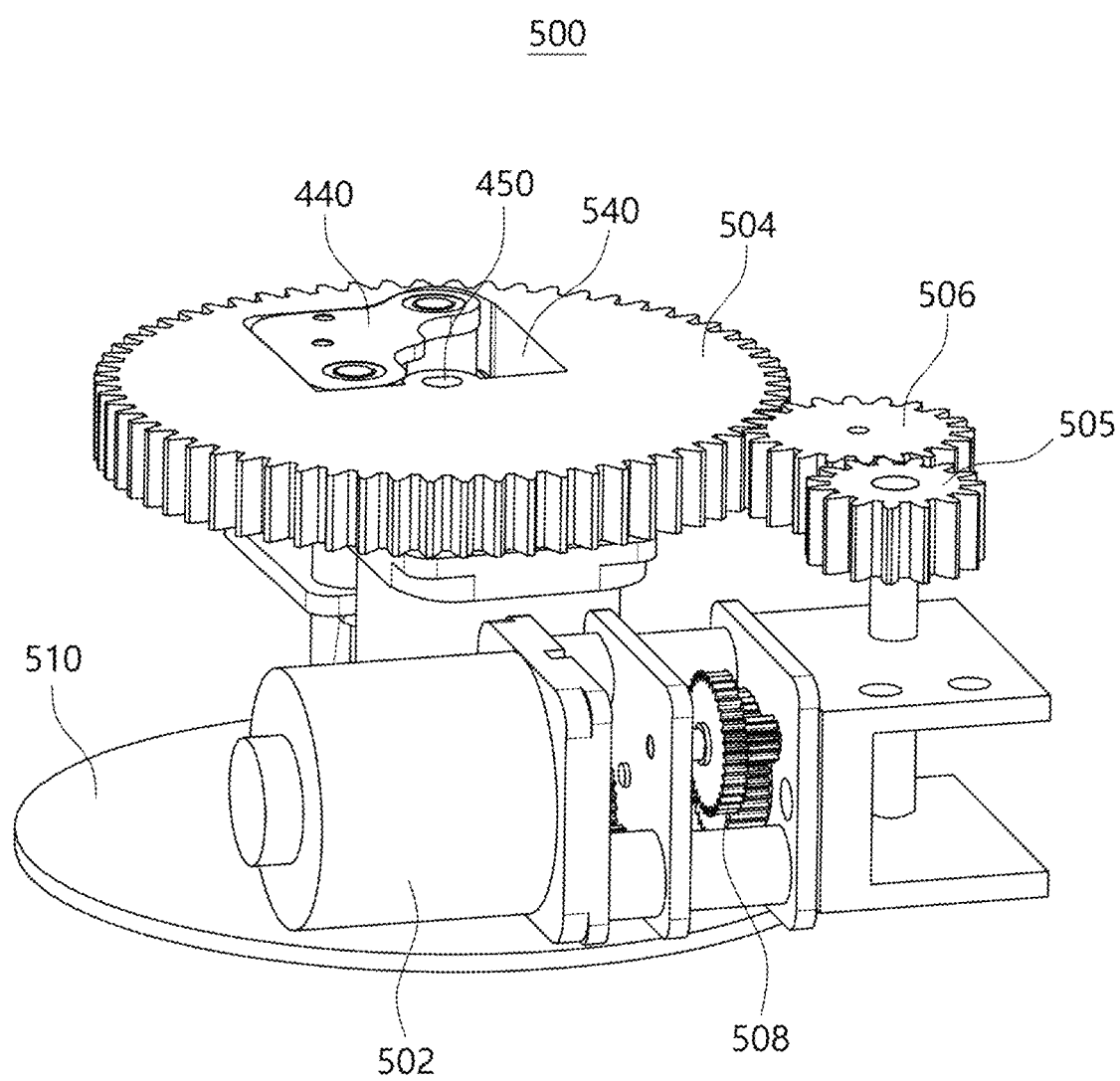
FIG. 13 illustrates the second drive mechanism from one side according to an embodiment.
Figure 14:
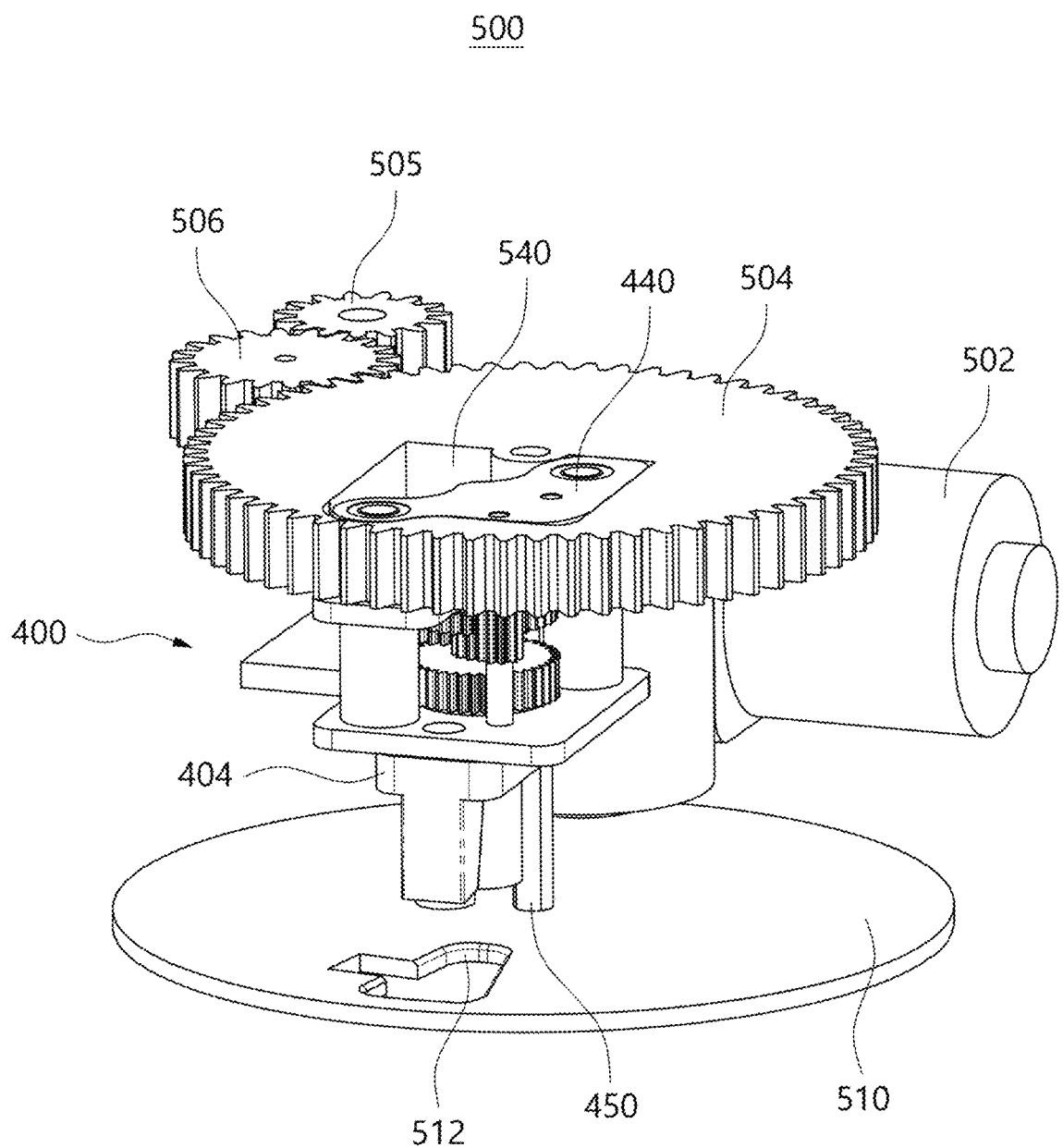
FIG. 14 illustrates the second drive mechanism from the other side according to an embodiment.

FIGS. 13 to 14 illustrate a second drive mechanism 500 according to an embodiment.

FIG. 13 illustrates the second drive mechanism from one side according to an embodiment, and FIG. 14 illustrates the second drive mechanism from the other side according to an embodiment.

Referring to FIGS. 13 to 14, the second drive mechanism 500 according to an embodiment may include a second driving motor 502, a main gear 504, one or more second connecting gears 505 and 506, and a lower plate 510.

First, the second driving motor 502 may operate by receiving a driving signal and power from the above-described PCB 203 (see FIG. 10). When the second driving motor 502 operates, the power of the second driving motor 502 may be transmitted to one or more second connecting gears 505 and 506 as a transmission gear 508 connected to the second driving motor 502 operates. One or more second connecting gears 505 and 506 that have received the power of the second driving motor 502 may engage and operate with the main gear 504. That is, one or more second connecting gears 505 and 506 transmit the power of the second driving motor 502 to the main gear 504, so that the main gear 504 may rotate around the shaft 450. Here, one or more second connecting gears 505 and 506 may perform a function of controlling the rotational speed of the main gear 504 according to a setting. It will be understood by those skilled in the art that in order to control the rotational speed of the main gear 504 according to the output of the second driving motor 502 or the driving signal, one or more second connecting gears 505 and 506 may have various design modifications of the gear structure, and it will be appreciated that such design variations are also incorporated within the spirit of this specification.

The main gear 504 may be coupled to the shaft 450. The shaft 450 may be coupled to the lower plate 510. That is, the main gear 504 and the lower plate 510 are coupled to both sides of the shaft 450 respectively so that the main gear 504 and the lower plate 510 may rotate to correspond to each other.

Here, the lower plate 510 may include a pressurizing opening part 512. The pressurizing part 404 may pressurize the microneedle patch 100 (see FIG. 3) through the pressurizing opening part 512. That is, as will be described later, when the microneedle patch 100 (see FIG. 3) is inserted into the applicator 200 (see FIGS. 3 to 10), the microneedle patch 100 may be positioned on the lower plate 510. At this time, when the pressurizing part 404 pressurizes the microneedle patch 100 (see FIG. 3), the microneedle may contact the user's body through the pressurizing opening part 512.

The first drive mechanism 400 and the second drive mechanism 500 may be operatively connected to each other through a mechanism connecting part 440.

Specifically, the first drive mechanism 400 may include the mechanism connecting part 440. The mechanism connecting part 440 may be coupled to the mechanism accommodating part 540 formed in the main gear 504. The mechanism connecting part 440 may also be connected to the shaft 450. The mechanism connecting part 440 may further include a shaft accommodating part (not shown), and the shaft 450 may be coupled to the shaft accommodating part (not shown).

As the mechanism connecting part 440 is connected to the mechanism accommodating part 540 and the shaft 450, when the main gear 504 rotates, the first drive mechanism 400 may rotate as a whole in response to the rotation of the main gear 504.

As such, the lower plate 510 and the first drive mechanism 400 may rotate to correspond to the main gear 504 according to the operation of the second driving motor 502.

Here, the applicator 200 (see FIG. 10) according to an embodiment may be set such that the initial position of the pressurizing part 404 of the first drive mechanism 400 corresponds to the pressurizing opening part 512 of the lower plate 510. For this reason, even when the main gear 504 rotates due to the operation of the second drive mechanism 500, the positions of the pressurizing part 404 and the pressurizing opening part 512 may correspond to each other. Thereafter, when the first drive mechanism 400 operates, the pressurizing part 404 pressurizes at least a portion of the microneedle patch 100 so that the microneedle can contact the user's body through the pressurizing opening part 512 and the opening of the lower cover 202.

Figure 15:
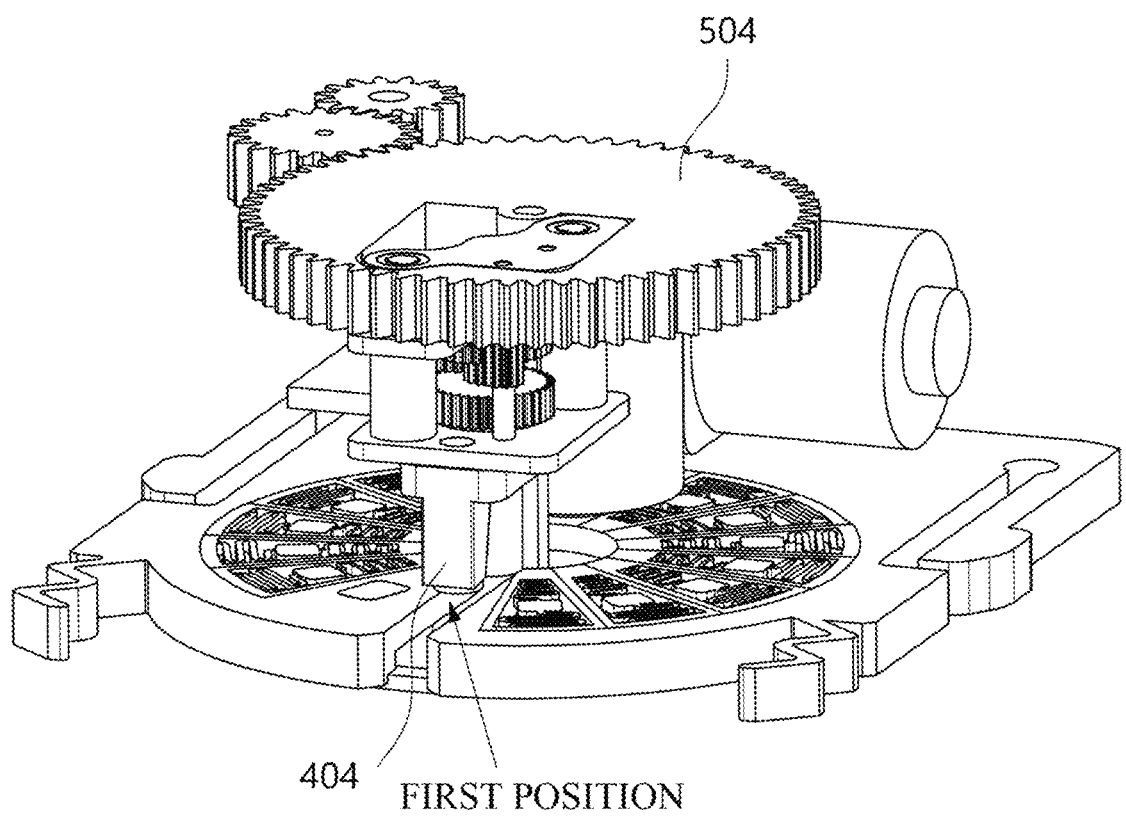
FIG. 15 illustrates an initial posture of a drive mechanism according to an embodiment.
Figure 16:
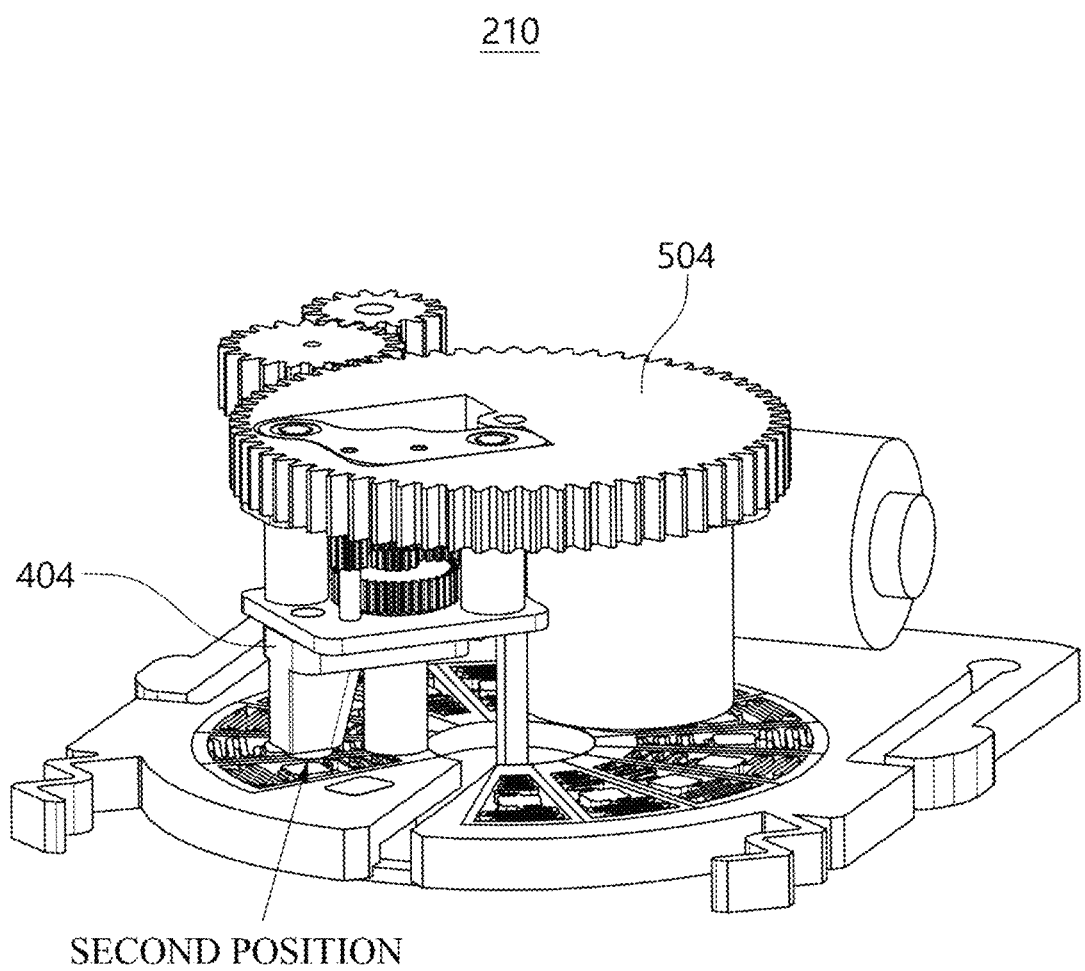
FIG. 16 illustrates a ready posture of a drive mechanism according to an embodiment.
Figure 17:
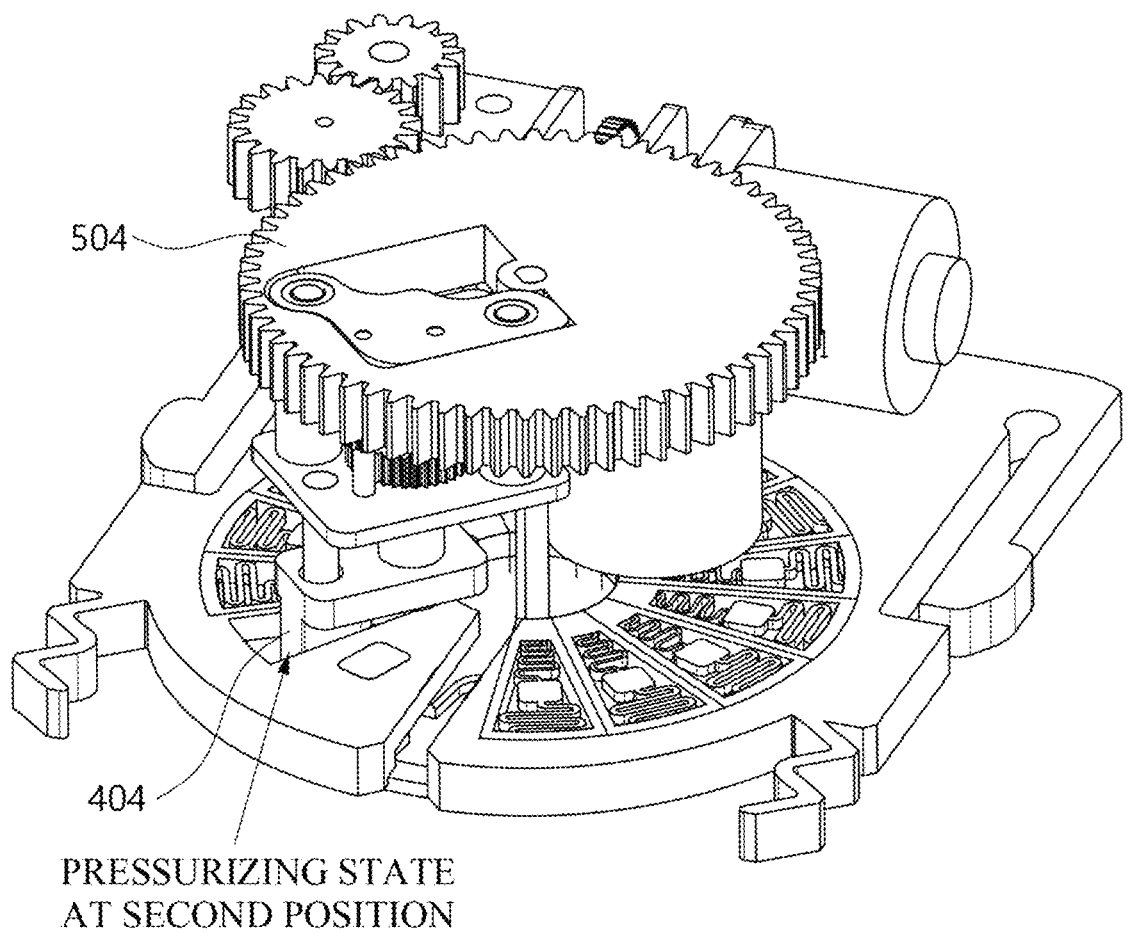
FIG. 17 illustrates a pressurizing posture of a drive mechanism according to an embodiment.

FIGS. 15 to 17 illustrate the operation of a drive mechanism according to an embodiment.

FIG. 15 illustrates an initial posture of a drive mechanism according to an embodiment, FIG. 16 illustrates a ready posture of a drive mechanism according to an embodiment, and FIG. 17 illustrates a pressurizing posture of a drive mechanism according to an embodiment.

The drive mechanism 210 according to an embodiment may change the posture to pressurize the microneedle patch 100. Specifically, the second drive mechanism 500 may change the position of the first drive mechanism 400 such that the first drive mechanism 400 can pressurize the microneedle patch 100 at a suitable position.

It will be described as a specific example with reference to the drawings.

Referring to FIG. 15, in the initial state (or standby state) of the applicator 200, the pressurizing part 404 may be located in a position corresponding to the auxiliary region 140 (see FIG. 4) of the microneedle patch 100. At this time, the pressurizing opening part 512 of the lower plate 510 may also be located at a position corresponding to the auxiliary region 140 (see FIG. 4).

In other words, it can be expressed that the pressurizing part 404 is located above the auxiliary region 140 (see FIG. 4), and the pressurizing opening part 512 may be located below the auxiliary region 140 (see FIG. 4).

That is, when the applicator 200 is in the standby state, if the position corresponding to the auxiliary region 140 (see FIG. 4) is expressed as the first position, both the pressurizing part 404 and the pressurizing opening part 512 may be located in the area corresponding to the first position.

As mentioned above, the auxiliary region 140 (see FIG. 4) prevents foreign substances from entering the microneedle patch 100 (see FIGS. 3 to 7) or the housing 201 (see FIG. 10) when the applicator 200 (see FIG. 10) is in a standby state, and correspondingly, the pressurizing part 404 and the pressurizing opening part 512 may be located at positions corresponding to the auxiliary region 140 (see FIG. 4) when the applicator 200 (see FIG. 10) is in a standby state.

Referring to FIGS. 16 to 17, the state in which the applicator 200 (see FIG. 10) has entered into an operating state is shown. When the applicator 200 (see FIG. 10) enters the operating state, the main gear 504 rotates according to the operation of the second drive mechanism 500. When the main gear 504 rotates, the position of the pressurizing part 404 rotating corresponding to the main gear 504 is also changed. The pressurizing part 404 rotates around the shaft 450 (see FIG. 14) according to the rotation of the main gear 504 to be located on a position corresponding to the microneedle body 151 (see FIG. 3). In this case, in response to the rotation of the main gear 504, the lower plate 510 also rotates, so that the pressurizing opening part 512 is also located at the bottom of the microneedle body 151 (see FIG. 3).

That is, the microneedle patch 100 (see FIG. 3) does not rotate, whereas the pressurizing part 404 and the pressurizing opening part 512 rotate with the microneedle patch 100 (see FIG. 3) interposed therebetween so that the pressurizing part 404 and the pressurizing opening part 512 will be placed in position corresponding to the microneedle body 151.

To put it another way, if the position corresponding to the microneedle body 151 (see FIG. 3) is expressed as the second position, it may also be said that when the applicator 200 (see FIG. 10) is in an operating state, the pressurizing part 404 and the pressurizing opening part 512 may also be placed in a region corresponding to the second position.

By placing the pressurizing part 404 and the pressurizing opening part 512 at positions corresponding to the microneedle body 151 (see FIG. 3), the microneedle is ready to contact the user's skin.

Referring to FIG. 17, the pressurizing part 404 executes translation movement vertically downward to the microneedle patch 100 (see FIG. 3) or the lower plate 510 according to the operation of the first drive mechanism 400. Here, as described above, the pressurizing part 404 may apply a predetermined pressure to the microneedle patch by moving a predetermined displacement. As a result, the microneedle body 151 (see FIG. 3) is pressurized, and the microneedle located at the lower part of the pressurized microneedle body 151 (see FIG. 3) may protrude to the outside of the pressurizing opening part 512. Accordingly, the microneedle located at the lower part of the microneedle body 151 (see FIG. 3) may be injected into the user's skin.

When the pressurizing part 404 returns to the initial position according to the driving of the first drive mechanism 400 after the microneedle is injected into the user's skin, the second drive mechanism 500 operates to return the pressurizing part 404 and the pressurizing opening part 512 present in the second position to the first position. Specifically, the main gear 504 rotates according to the operation of the second driving motor 502, and the pressurizing part 404 and the pressurizing opening part 512 rotate around the shaft 450 in response to the rotation of the main gear 504, thereby returning to the first position.

When the pressurizing part 404 and the pressurizing opening part 512 are returned to the first position, the applicator 200 enters the standby state. As will be described later, when the applicator 200 enters the operating state again, the second drive mechanism 500 operates to position the pressurizing part 404 and the pressurizing opening part 512 on the microneedle body corresponding to the third position. Here, the third position will mean a position different from the microneedle body corresponding to the second position. Also, the microneedle body corresponding to the second position and the microneedle body corresponding to the third position may be adjacent to each other. Also, a distance from the first location to the third location may be longer than a distance from the first location to the second location.

Figure 18:
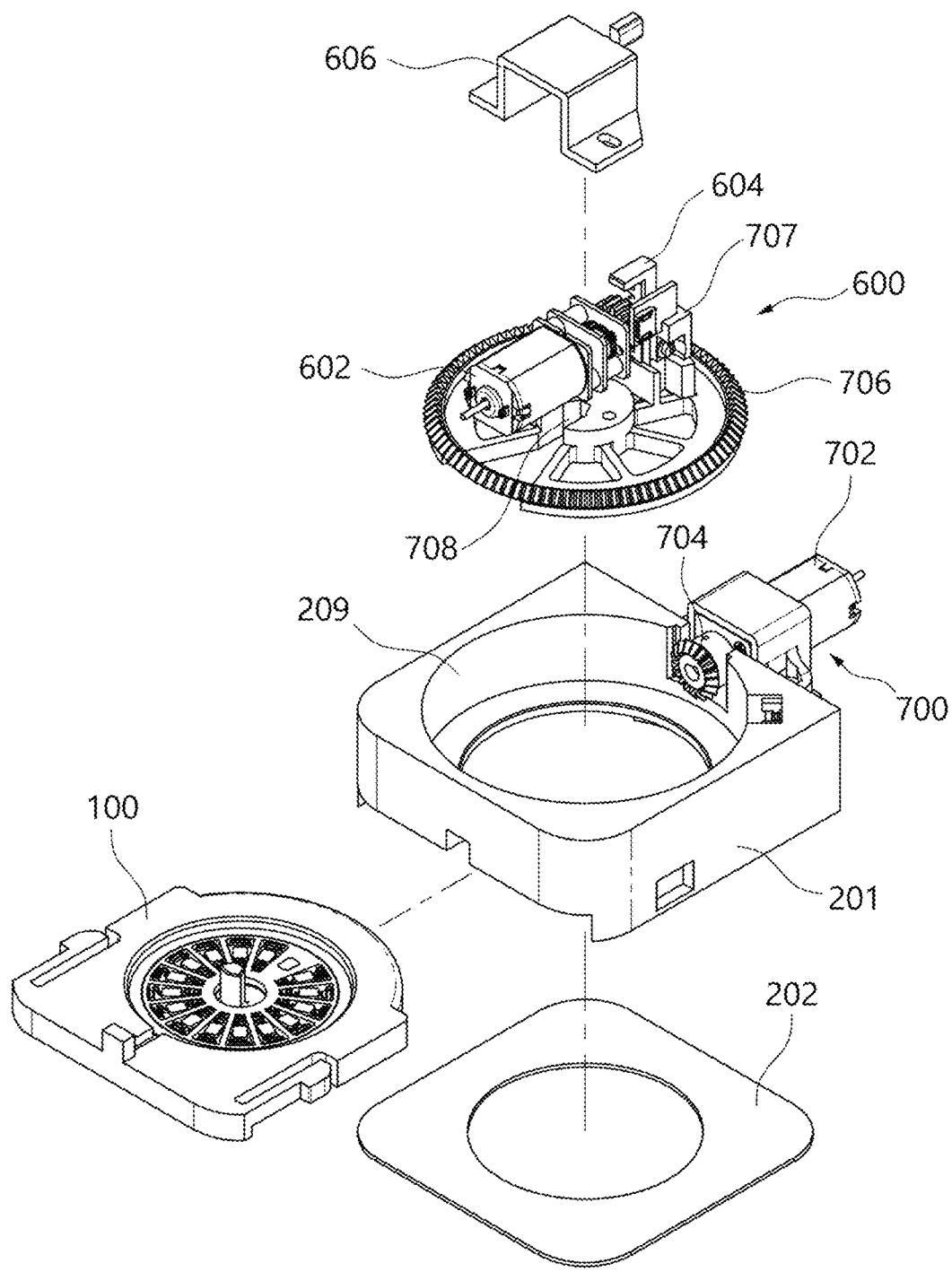
FIG. 18 is a half exploded view illustrating a drive mechanism according to another embodiment.
Figure 19:
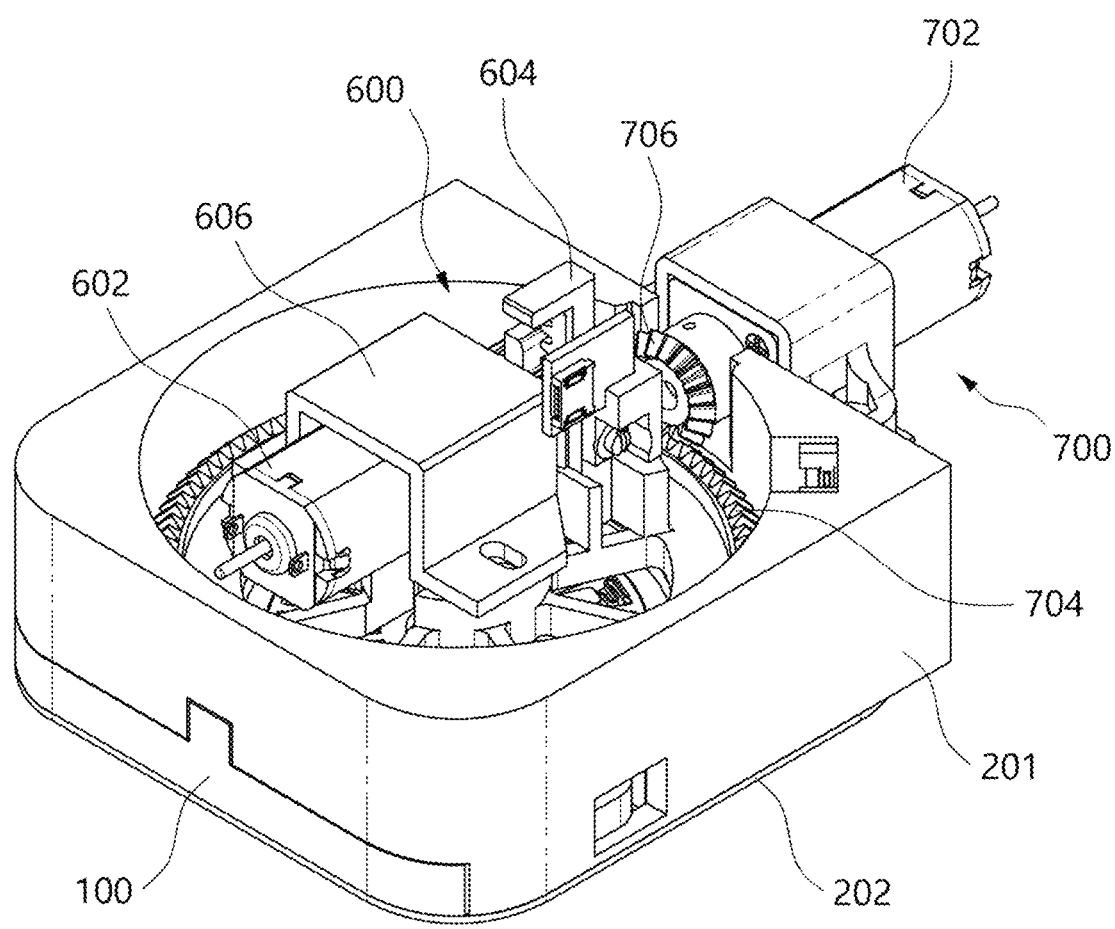
FIG. 19 illustrates a state in which a drive mechanism is connected according to another embodiment.

FIGS. 18 and 19 illustrate a drive mechanism according to another embodiment.

FIG. 18 is a half exploded view illustrating a drive mechanism according to another embodiment, and FIG. 19 illustrates a state in which a drive mechanism is connected according to another embodiment.

Referring to FIG. 18, the applicator 200 according to an embodiment may include a third drive mechanism 600 and a fourth drive mechanism 700.

The third drive mechanism 600 is functionally similar to the first drive mechanism 400 (see FIGS. 13 to 17), but there is a difference in the mechanism structure thereof. In the description of this specification, only the differences between the third drive mechanism and the first drive mechanism 400 (see FIGS. 13 to 17) will be described, and it will be understood that other descriptions may refer to the contents regarding the first driving mechanism 400.

The fourth drive mechanism 700 is functionally similar to the second drive mechanism 500 (see FIGS. 13 to 17), and there is a difference in the mechanism structure thereof. Again, differences between the second drive mechanism and the fourth drive mechanism 700 will be mainly described.

The third drive mechanism 600 according to an embodiment may include a third driving motor 602 and a transmission gear (not shown) and a rack gear 604.

Since the description of the third driving motor 602 is similar to the above-description of the first driving motor 402, a detailed description thereof will be omitted.

Unlike the structural relationship between the first drive mechanism 400 and the second drive mechanism 500, the third drive mechanism 600 may be mainly located on top of the fourth drive mechanism 700. Specifically, the third driving motor 602 may be disposed on top of the frame gear 706. The rack gear 604 may move in a downward direction of the applicator 200 during operation through an opening formed in the frame gear 706. Specifically, the rack gear 604 may be mounted on a rack gear accommodating part 707 formed on the frame gear 706.

When the third driving motor 602 operates, one or more transmission gears (not shown) may transmit the power of the third driving motor 602 to the rack gear 604. The rack gear 604 receiving power from the third driving motor 602 executes vertical translation movement in the rack gear accommodating part 707, thereby pressurizing the microneedle body 151 (see FIG. 3). Here, a separate pressurizing region may be set in the rack gear 604, or an additional pressurizing portion may be added.

The third driving motor 602 and the one or more transmission gears may be protected through a protection part 606.

The fourth drive mechanism 700 includes a fourth driving motor 702, an auxiliary gear 704 and a frame gear 706.

The description of the fourth driving motor 702 is similar to the description of the second driving motor 502 and thus will be omitted.

The auxiliary gear 704 receives power from the fourth driving motor 702. The auxiliary gear 704 engages with the frame gear 706. The auxiliary gear 704 transmits the power of the fourth driving motor 702 to the frame gear 706 and performs a function of controlling the rotation speed of the frame gear 706.

The frame gear 706 is mounted on the frame gear accommodating part 209 inside the housing 201. The frame gear accommodating part 209 may be formed to correspond to the shape of the frame gear 706. The frame gear 706 may be accommodated in the frame gear accommodating part 209, and may rotate by the power of the fourth driving motor 702 received through the auxiliary gear 704.

Here, as the rack gear accommodating part 707 is formed on top of the frame gear 706, when the frame gear 706 rotates as a whole, the rack gear accommodating part 707 and the rack gear 604 accommodated in the rack gear accommodating part 707 also rotate in response to the rotation of the frame gear 706. Through this, the rack gear 604 may move from the first position to the second position as described above.

In addition, a flat plate accommodating part 708 may be formed in the central portion of the frame gear 706. The flat plate accommodating part 708 accommodates the aforementioned fixing portion 1005, and as the fixing portion 1005 is coupled to the flat plate accommodating part 708, the plate 1004 may rotate together in response to the rotation of the frame gear 706.

Similar to the relationship between the pressurizing part 404 (see FIGS. 13 to 17) and the pressurizing opening part 512 (see FIGS. 13 to 17) described above, the initial positions of the rack gear 604 and the plate opening 1006 (see FIG. 9) may also correspond. In response to the rotation of the frame gear 706, the rack gear 604 and the plate opening 1005 may also rotate together. Due to this, as the frame gear 706 rotates, the rack gear 604 and the flat plate opening 1006 may be positioned on at least one or more microneedle bodies 151 (see FIG. 3).

In summary, according to the operation of the fourth drive mechanism 700, the rack gear 604 and the flat plate opening 1006 are positioned in the microneedle body 151 (see FIG. 3). Thereafter, the rack gear 604 pressurizes the microneedle body 151 (see FIG. 3) according to the operation of the third drive mechanism 600. The microneedles formed in the pressurized microneedle body 151 (see FIG. 3) protrude outward through the flat plate opening 1006, so that the microneedles can be injected into the user's body.

FIGS. 20A, 20B, 21A, and 21B illustrate a drive mechanism according to another embodiment.

Figure 20A:
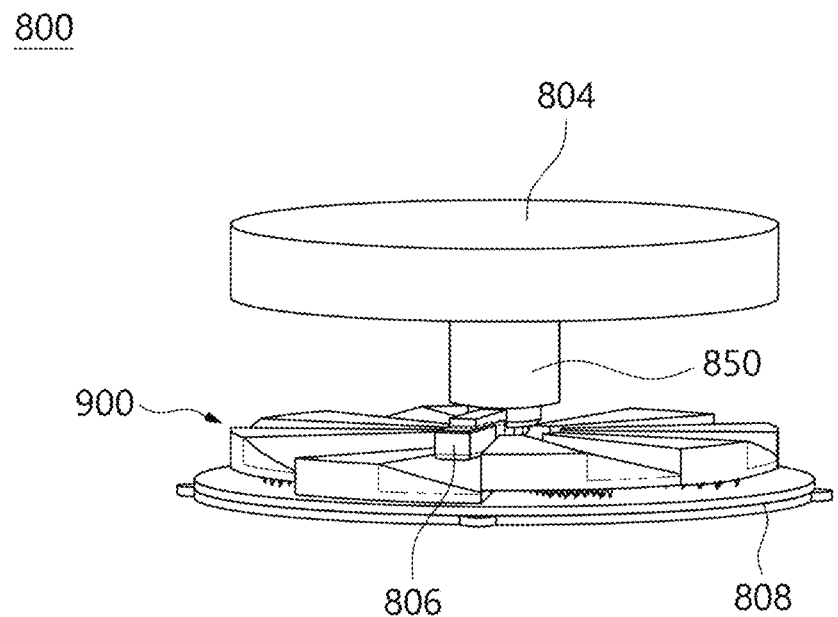
FIGS. 20A and 20B illustrate a drive mechanism according to yet another embodiment.
Figure 20B:
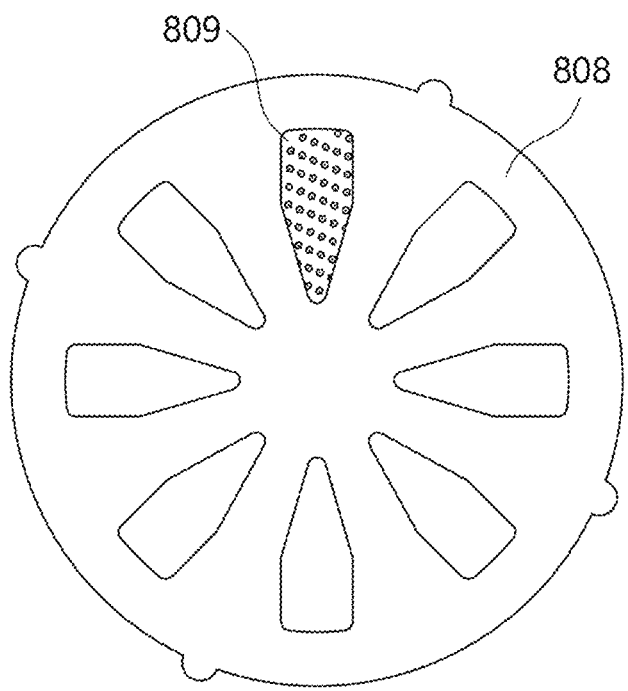
Figure 21A:
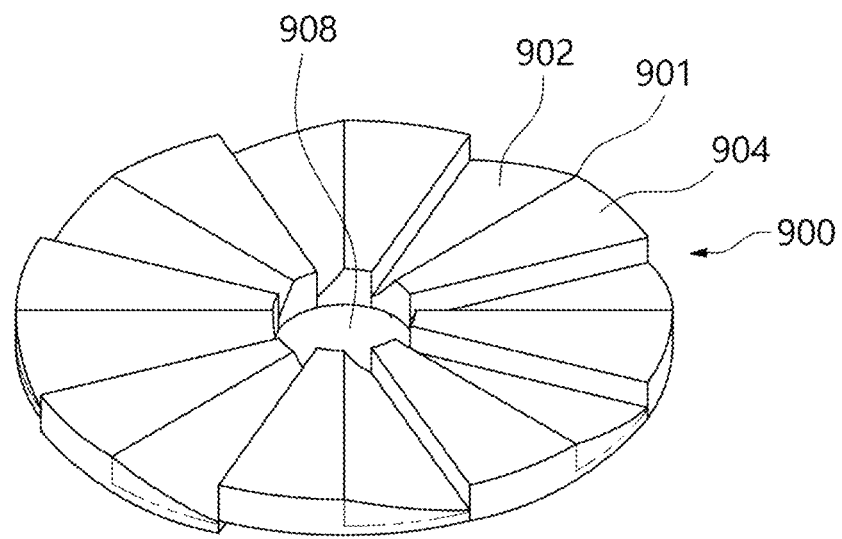
FIGS. 21A and 21B illustrate a wedge-shaped microneedle patch used in the drive mechanism according to yet another embodiment.
Figure 21B:
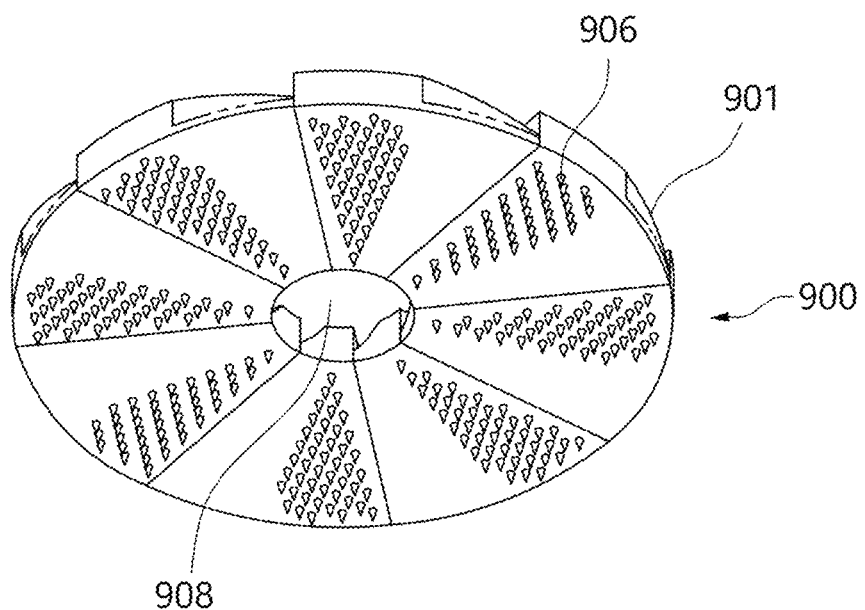

FIGS. 20A and 20B illustrate a drive mechanism according to yet another embodiment, and FIGS. 21A and 21B illustrate a wedge-shaped microneedle patch used in the drive mechanism according to yet another embodiment.

Referring to FIGS. 20A and 20B, the applicator 200 (see FIG. 10) according to an embodiment may be implemented through a fifth drive mechanism 800.

FIG. 20A is a front view of the fifth drive mechanism, and FIG. 20B is a bottom view of the fifth drive mechanism.

The fifth drive mechanism 800 may include a fifth driving motor (not shown), a second main gear 804, a second pressurizing part 806, and a second lower plate 809. The fifth drive mechanism 800 is preferably operated in interaction with the microneedle patch 900 having a wedge shape.

The operation of the fifth drive mechanism 800 is almost similar to the operation of the second drive mechanism 500. Since the operational relationship between the main gear 504 and the lower plate 510 may be applied to the operational relationship between the second main gear 804 and the second lower plate 808, a detailed description thereof will be omitted.

The fifth drive mechanism 800 may also include a second pressurizing part 806. Unlike the first and second drive mechanisms 400 and 500, the second pressurizing part 806 is coupled to the second shaft 850. For this reason, the second pressurizing part 806 may rotate together with the second shaft 850 in response to the rotation of the second main gear 804.

A microneedle patch having a wedge shape will be described with reference to FIGS. 21A and 21B.

Referring to FIGS. 21A and 21B, the microneedle patch 900 having a wedge shape may include a plurality of wedge bodies 901. Here, the wedge body 901 may include an inclined surface 902 and a flat surface 904 on one surface. A microneedle 906 storing a drug may be formed on the opposite surface of each wedge body 901. The microneedles 906 may be formed in a region corresponding to the flat surface 904. The microneedle patch 900 may have a second shaft accommodating part 908 in which the second shaft 850 may be accommodated in the center thereof.

A specific driving example of the fifth drive mechanism 800 will now be described with reference to FIGS. 20A, 20B, 21A, and 21B.

When the fifth driving motor (not shown) operates and the second main gear 804 rotates, the second lower plate 808 and the second pressurizing part 806 connected to the second main gear 804 through the second shaft 850 may rotate together.

At this time, the microneedle patch 900 does not rotate, and the second pressurizing part 806 may move along the surface of the inclined surface 902. As the second pressurizing part 806 moves along the inclined surface 902, the microneedle patch 900 may be pressed downward. In this case, the second lower plate 808 may also be rotated, so that the second pressurizing opening part 809 may be located in the area where the microneedle 906 is formed.

When the second pressurizing opening part 809 is positioned in the region where the microneedle 905 is formed, the second pressurizing part 806 moves on the flat surface 904. When the second pressurizing part 806 moves on the flat surface 904 and pressurizes the wedge body 901, a microneedle 906 located on the opposite surface of the flat surface 904 may protrude through the second v 809 to inject a drug to the user.

After moving on the flat surface 904, the second pressurizing part 806 may be positioned on another wedge body 901 formed in the microneedle patch 900. Specifically, as the second main gear 804 further rotates, the second pressurizing part 806 may be located on the inclined surface 902 of the wedge body 901 different from the wedge body already pressurized. In this case, the second pressurizing opening part 809 may be located on the opposite surface of the microneedle patch 900 corresponding to the inclined surface 902 in which the microneedle 906 is not formed. Thus, it is possible to prevent foreign substances from entering the microneedle 906.

In the above, the drive mechanism of the applicator 200 according to various embodiments was described.

Hereinafter, the overall operation of the applicator 200 according to the embodiment will be described, with the description focusing mainly on electrical control.

Figure 22:
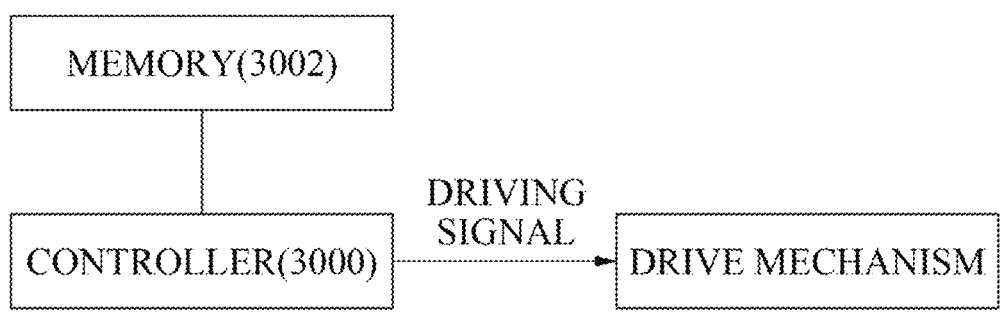
FIG. 22 illustrates a control configuration of an applicator according to an embodiment.

FIG. 22 illustrates a control configuration of an applicator according to an embodiment.

According to an embodiment, the applicator may include a controller 3000 and a memory 3002. The controller 3000 and the memory 3002 may be implemented through a circuit design of the above-described PCB 203 (see FIG. 10).

The memory 3002 may store various types of information. Various data may be temporarily or semi-permanently stored in the memory 3002. The memory 3002 may include, for example, a hard disk, SSD, flash memory, ROM, RAM, and the like. The memory 3002 may store an operating program for driving the applicator 200 or various data necessary for the operation of the applicator.

For example, the memory 3002 may store structural information about the microneedle patch. Specifically, the memory 3002 may store information about the spacing between each microneedle body included in the microneedle patch. Also, the memory 3002 may store information on the positional relationship between each microneedle body included in the microneedle patch and the auxiliary region 151 (see FIG. 3).

As another example, the memory 3002 may store output information of the drive mechanism 210 (see FIG. 10) corresponding to structural information about the microneedle patch.

Specifically, the memory 3002 may include, as described above, output information of a drive mechanism for moving the pressurizing part 404 from the first position to the second position and output information of the drive mechanism for the pressurizing part 404 to pressurize the microneedle patch.

In addition to this, it will be apparent to those skilled in the art that all information for the operation of the applicator described above or to be described later in this specification may be stored in advance in the memory 3002.

The controller 3000 may control the overall operation of the applicator 200. For example, the controller 3000 may control the operation of the drive mechanism 210 by transmitting a driving signal to the drive mechanism 210 (see FIG. 10).

The applicator 200 according to an embodiment may be set to inject the drug through the microneedle to the user at a predetermined time. The predetermined time may be set by the user or may be predetermined for a specific drug.

Figure 23:
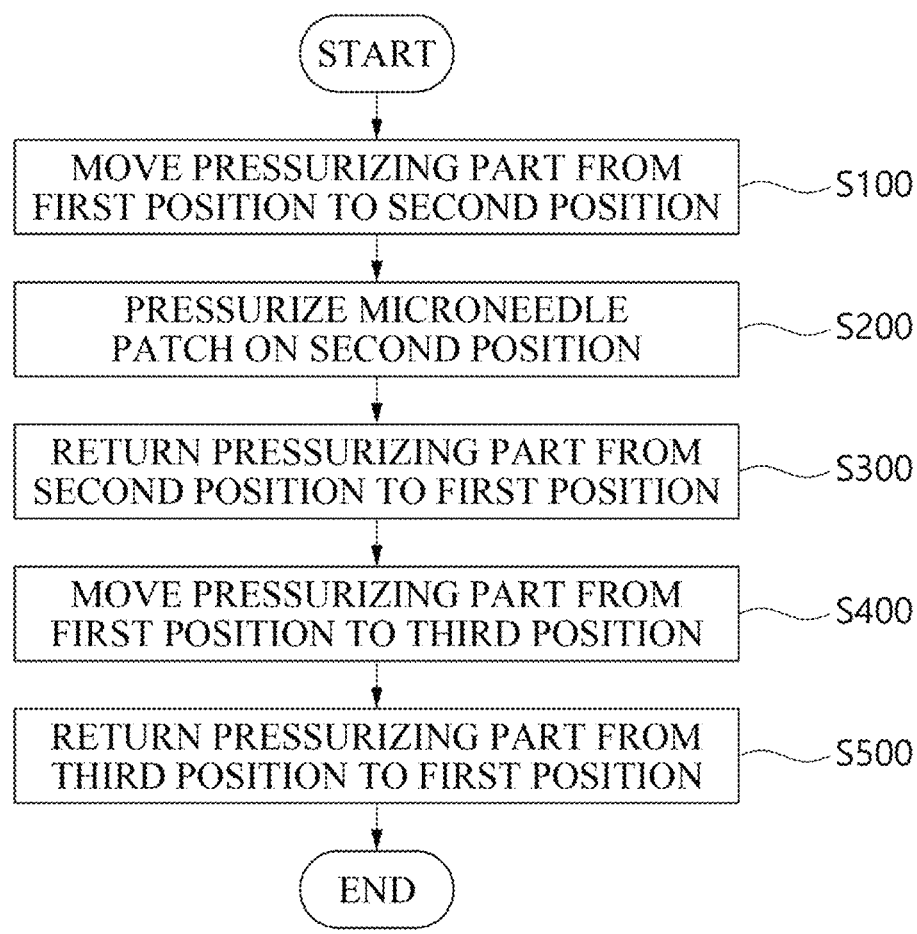
FIG. 23 is a flowchart illustrating a method of controlling an applicator performed by a controller according to an embodiment.

FIG. 23 is a flowchart illustrating a method of controlling an applicator performed by a controller according to an embodiment.

According to an embodiment, the control method of the applicator includes the steps of moving the pressurizing part from the first position to the second position S100, pressurizing the microneedle patch with the pressurizing part at the second position S200, returning the pressurizing part from the second position to the first position S300, moving the pressurizing part from the first position to the third position S400, and returning the pressurizing part from the third position to the first position S500.

According to an embodiment, the controller 3000 may control the second drive mechanism 500 so that the pressurizing part 404 is positioned at the first position S100. Specifically, when the controller 3000 transmits a driving signal to the second drive mechanism 500, the second drive mechanism 500 operates as much as a predetermined output, and due to this, as the main gear 504 rotates, the pressurizing part 404 may move from the first position to the second position.

When the pressurizing part 404 moves from the first position to the second position, the controller 3000 may control the first drive mechanism 400 for the pressurizing part 404 to pressurize the microneedle patch S200. Specifically, when the controller 3000 sends a driving signal to the first drive mechanism 400, the first drive mechanism may operate according to a predetermined output so that the pressurizing part 404 may pressurize the microneedle patch 100.

After the pressurizing part 404 pressurizes the microneedle patch 100, the controller 3000 may control the second drive mechanism 500 so that the pressurizing part 404 is returned from the second position to the first position S300. Specifically, when the controller 3000 transmits a driving signal, the second drive mechanism operates by a predetermined output and, due to this, the main gear 504 rotates and accordingly, the pressurizing part 404 may be returned from the second position to the first position.

After the pressurizing part 404 is returned to the first position, the controller 3000 may control the second drive mechanism 400 to move the pressurizing part 404 from the first position to the third position S400. Specifically, when the controller 3000 sends a drive signal to the second drive mechanism 400, the second drive mechanism may be operated according to the predetermined output to move the pressurizing part 404 from the first position to the third position. When the pressurizing part 404 moves to the third position, the controller 3000 may control the first drive mechanism so that the pressurizing part 404 pressurizes the microneedle body corresponding to the third position.

The microneedle patch 100 according to an embodiment is not allowed to be reused. Also, as described above, one microneedle body 151 may store one dose of drug. Therefore, the applicator 200 may inject the drug stored in one microneedle body to the user at the second position, and then inject the drug stored in the other microneedle body to the user at the third position. Thus, it will be apparent that the drug stored in the microneedle body present in the fourth position rather than the third position may be injected to the user thereafter.

After the pressurizing part 404 pressurizes the microneedle body at the third position, the controller 300 may control the second drive mechanism 500 to return the pressurizing part 404 from the third position to the first position.

As such, as the controller 3000 controls the drive mechanism to return the pressurizing part 404 to the initial position (first position) after pressurizing the microneedle body at various positions, the pressurizing opening part 512, which rotates corresponding to the pressurizing part 404, is also returned to its initial position, when the applicator is in the standby state, the pressurizing opening part 512 may be located in the auxiliary region 140 (see FIG. 3). Due to this, there is an effect that the contamination of the microneedle patch, which is vulnerable even to slight contamination, can be prevented.

Figure 24:
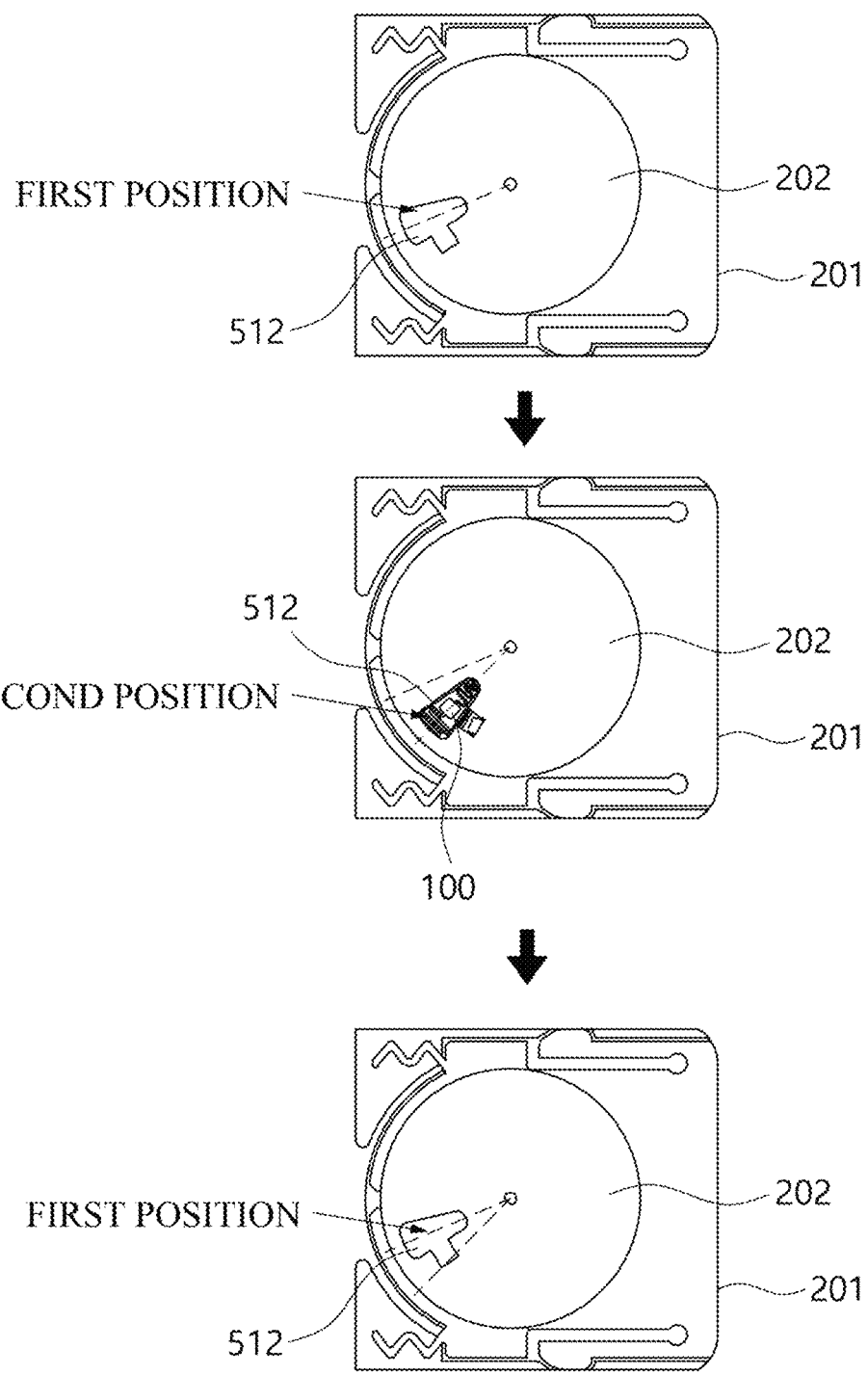
FIG. 24 illustrates the first drug injection operation of an applicator according to an embodiment viewed from the back of the applicator.
Figure 25:
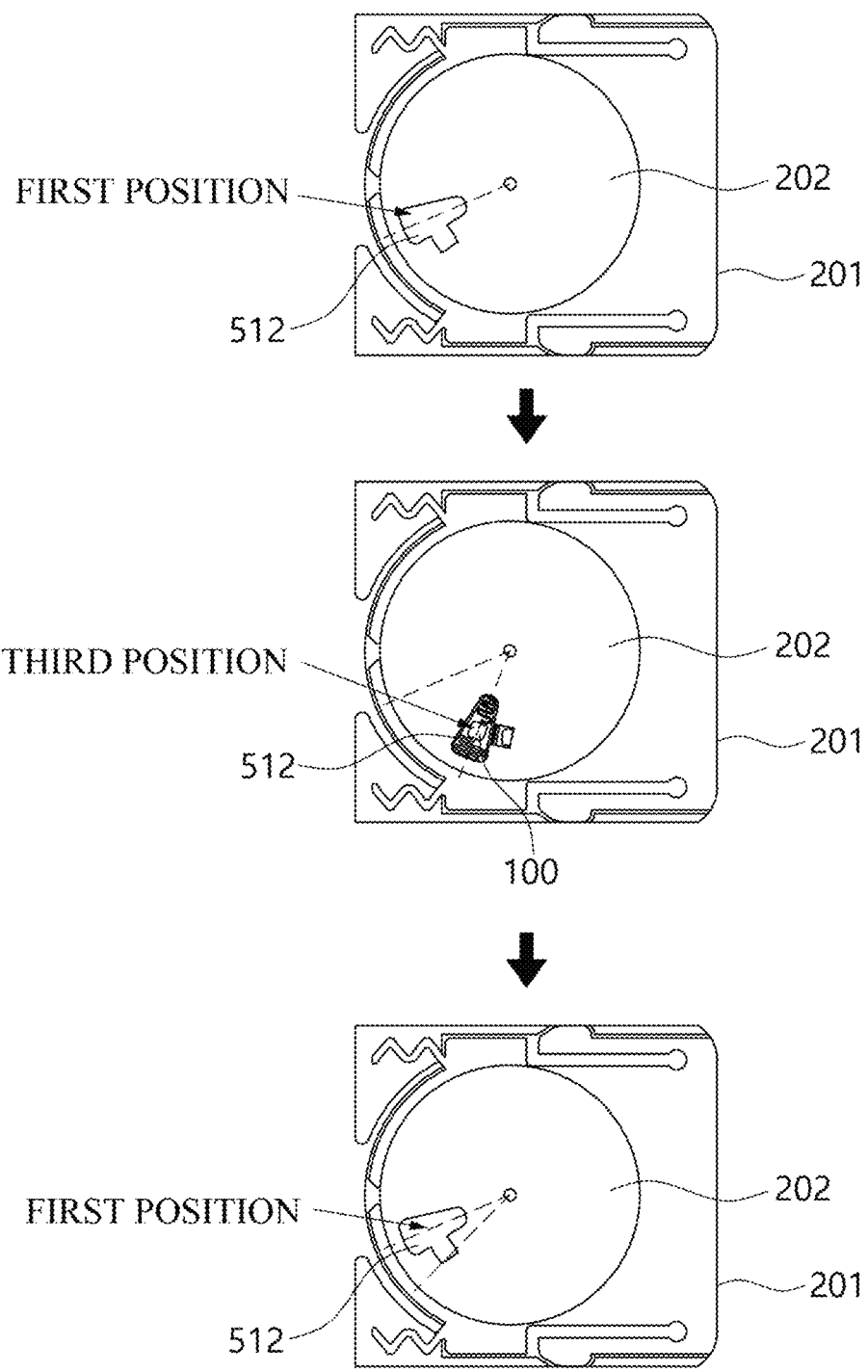
FIG. 25 illustrates the second drug injection operation of an applicator according to an embodiment viewed from the back of the applicator.

FIGS. 24 and 25 are views of the operating process of the applicator according to an embodiment from the back of the applicator.

FIG. 24 illustrates the first drug injection operation of an applicator according to an embodiment viewed from the back of the applicator, and FIG. 25 illustrates the second drug injection operation of an applicator according to an embodiment viewed from the back of the applicator.

Referring to FIG. 24, in the standby state of the applicator, the pressurizing opening part 512 is placed at the first position. At this time, the pressurizing opening part 512 is placed in the auxiliary area 140, so that the auxiliary area prevents foreign substances from entering from the outside.

Thereafter, when the applicator operates, the pressing opening 512 may move from the first position to the second position. When the pressurizing opening part 512 moves from the first position to the second position, a body portion 151 of the microneedle patch is positioned in the pressurizing opening part 512. Here, the microneedle may be exposed to the outside, and the microneedle may contact the user's body by the pressurization of the pressurizing part 404.

After injection of the drug, the pressurizing opening part 512 is returned to the first position again, and the applicator enters the standby state. Consequently, the auxiliary region 140 prevents foreign substances from being introduced from the outside and prevents the microneedle patch from being contaminated.

Referring to FIG. 25, a second drug injection operation is shown.

When the applicator is operated from the standby state, the pressurizing opening part 512 may be moved from the first position to the third position instead of the second position. The third position may be expressed as a position corresponding to a microneedle body different from the microneedle body corresponding to the second position. When the drug injection at the third position is completed, the pressurizing opening part 512 may be returned to the initial position (the first position).

As such, when a plurality of drug injections are performed for one microneedle patch, due to the drive mechanism, only drug injection into one microneedle body per one operation is performed, so that a fixed amount of drug injection is possible. Also, when the applicator enters the standby state after drug injection, the pressurizing opening part 512 is returned to its initial state to prevent contamination of the microneedle patch.

In the above, the drug injection operation of the microneedle patch and the applicator was mainly examined.

However, accurate injection of the drug may be performed when the applicator is properly mounted on the user's body and operated. To this end, the applicator according to an embodiment may further include a touch sensor for determining whether the applicator is correctly mounted on the user.

Figure 26:
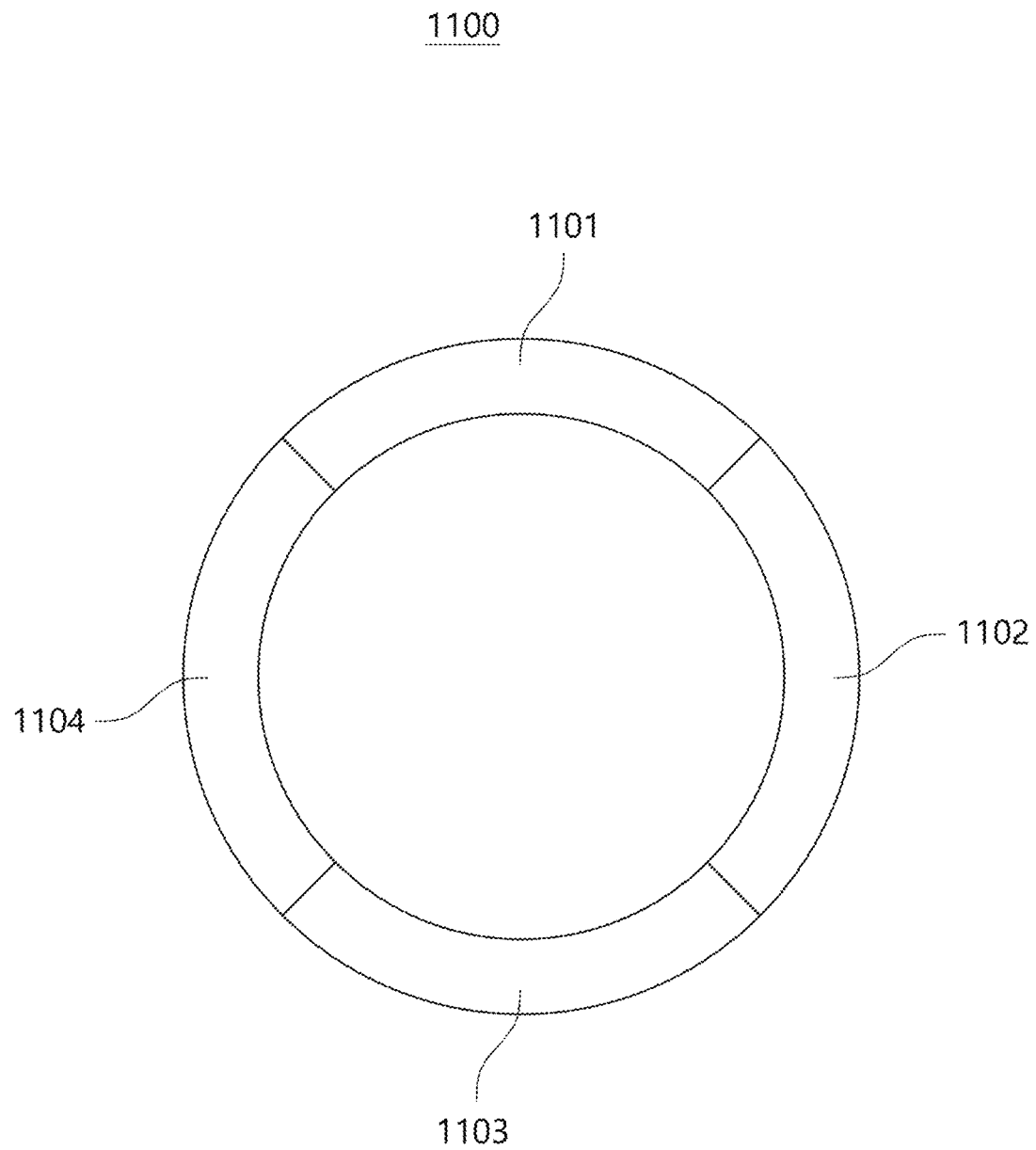
FIG. 26 illustrates a touch sensor according to an embodiment.

FIG. 26 illustrates a touch sensor according to an embodiment.

According to an embodiment, the applicator 200 may further include a touch sensor 1100. The touch sensor 1100 may be attached to a lower cover 202. Specifically, the touch sensor 1100 may be attached to the outside or the inside of the lower cover 202. Also, the touch sensor 1100 may have a circular or annular shape corresponding to the shape of the lower cover 202. In addition, the touch sensor 1100 may be formed integrally with the lower cover 202.

For example, the touch sensor may be implemented as a capacitive touch sensor.

The touch sensor 1100 may be divided into a plurality of zones. In the drawing, the touch sensor divided into first to fourth zones 1101, 1102, 1103, and 1104 is illustrated by way of example. However, this is only an example, and it will be understood that a touch sensor divided into more or fewer zones may also be used.

When an object contacts all or some areas 1101, 1102, 1103, 1104 of the touch sensor 1100, the amount of current flowing for each zone is changed, and due to this, the controller 3000 can determine whether the applicator is correctly mounted on the user's body.

FIGS. 27A and 27B are graphs illustrating an electrical signal measured by a touch sensor according to the mounting state of an applicator.

The applicator may determine whether the applicator is properly mounted prior to actuating the drive mechanism. Specifically, the controller 3000 may determine whether the applicator is correctly mounted on the user's body based on an electrical signal value flowing through the touch sensor 1100.

In the graph shown in FIGS. 27A and 27B, the x-axis means time. Units of measure can be sec, ms, us, ns, etc., as well as all units of measure for time. It will be appreciated that the y-axis may be an electrical signal including a sensor output or a capacitance value, and any unit of measure representing them may be used. Although the measurement unit is not clearly disclosed in the graphs of FIGS. 27A and 27B, all measurement units representing time and electrical signals may be used.

FIG. 27A shows a case in which the applicator according to an embodiment is suitably mounted to the user's body. Referring to FIG. 27A, it is shown that the amount of current measured in each region 1101, 1102, 1103, 1104 of the touch sensor 1100 is equal to or greater than a threshold value.

As such, when the value of the current measured in each zone of the touch sensor 1100 is equal to or greater than the threshold value, the controller 3000 may determine that the applicator is properly mounted on the user's body. If it is determined that the applicator is properly mounted, the controller 3000 may transmit a driving signal for drug injection to the drive mechanism. However, this is only an example and when the number of zones included in the touch sensor 1100 is large, even when a current greater than a threshold value flows in more than a predetermined number of zones, the controller 3000 may determine that the applicator is properly mounted on the user's body. It will be understood that various examples that may be modified in addition to this may be incorporated into the spirit of the present disclosure.

FIG. 27B shows a case in which the applicator according to an embodiment is not properly mounted on the user's body. Referring to FIG. 27B, only the current value flowing in the first region 1101 included in the touch sensor 1100 was measured as a current value greater than or equal to the threshold value, and in the case of the remaining regions 1102, 1103, 1104, the current values were measured as less than of equal to the threshold. In this case, the controller 3000 may determine that the applicator is not properly mounted on the user's body. If it is determined that the applicator is not properly mounted on the user's body, the controller 3000 may not transmit a driving signal for actuating the drive mechanism. Also, the controller 3000 may generate an indication signal reflecting that the applicator is not properly worn, and may provide it to an outside (user) through a display.

In the above, the configuration and features of the present disclosure have been described based on the embodiments according to the present disclosure, however, the present disclosure is not limited thereto and it should be apparent to those skilled in the art to which the present disclosure pertains that various changes or modifications can be made within the spirit and scope of the present disclosure, and thus such changes or modifications fall within the scope of the appended claims.

What is claimed is:

1. A microneedle patch comprising:
a body in which at least one opening is formed;
a microneedle body disposed in the opening and comprising at least one microneedle formed therein, the microneedle body comprising a first side and a second side opposing each other; and
a connector connecting the microneedle body and the body, wherein the connector includes a first connector and a second connector,
wherein the first connector connects the first side of the microneedle body and the body,
wherein the second connector connects the second side of the microneedle body and the body,
wherein the first connector and the second connector are formed in a spring structure having a different widths and pitches from each other,
wherein in response to an external force being applied in the first direction on the microneedle body located at a first position, the microneedle body is configured to move to a second position by an elastic deformation of the connector so as to administer a drug in the microneedle to a user's skin, and
wherein the microneedle body moved to the second position is configured to move in a second direction opposite to the first direction.

2. The microneedle patch of claim 1, wherein the body further comprises an auxiliary region in which the opening is not formed, and
wherein, in response to a wearable device including the microneedle patch being in a standby state, the auxiliary region is configured to serve to block an internal structure of the wearable device from an outside.

3. The microneedle patch of claim 2, wherein the microneedle body is configured to move in the first direction so as to administer the drug through an opening part of the wearable device, and
wherein the microneedle patch is configured to rotate for the microneedle body to be located on a position corresponding to the opening part of the wearable device.

* * * * *